US006967246B2

(12) United States Patent
Swanson et al.

(10) Patent No.: US 6,967,246 B2
(45) Date of Patent: Nov. 22, 2005

(54) MICROBIAL SWOLLENIN PROTEIN, DNA SEQUENCES ENCODING SUCH SWOLLENINS AND METHOD OF PRODUCING SUCH SWOLLENINS

(75) Inventors: Barbara A. Swanson, San Francisco, CA (US); Michael Ward, San Francisco, CA (US); Merja Penttilä, Helsinki (FI); Jaakko Pere, Vantaa (FI); Markku Saloheimo, Helsinki (FI)

(73) Assignee: Genencor International, Inc., Palo Alto, CA (US)

( * ) Notice: Subject to any disclaimer, the term of this patent is extended or adjusted under 35 U.S.C. 154(b) by 500 days.

(21) Appl. No.: 10/197,294

(22) Filed: Jul. 17, 2002

(65) Prior Publication Data

US 2003/0104546 A1 Jun. 5, 2003

Related U.S. Application Data

(60) Division of application No. 09/112,498, filed on Jul. 9, 1998, now Pat. No. 6,458,928, which is a continuation-in-part of application No. 08/893,766, filed on Jul. 11, 1997, now abandoned.

(51) Int. Cl.[7] .................. C07H 21/02; C07H 21/04; C12P 21/06; C07K 14/00; A61K 38/00
(52) U.S. Cl. .................. 536/23.74; 536/23.1; 536/23.7; 536/24.32; 435/69.1; 435/252.3; 435/320.1; 435/262; 435/254.1; 435/254.3; 435/254.6; 530/350; 530/300
(58) Field of Search .................. 536/23.1, 23.7, 536/23.74, 24.32; 435/262, 69.1, 252.3, 320, 254.1, 254.3, 254.6; 530/350, 300

(56) References Cited

U.S. PATENT DOCUMENTS

| 5,246,853 A | 9/1993 | Clarkson et al. ............ 435/263 |
| 5,475,101 A | 12/1995 | Ward et al. ............... 536/23.74 |

FOREIGN PATENT DOCUMENTS

| WO | WO 92/06209 | 4/1992 |
| WO | WO 93/05226 | 3/1993 |
| WO | WO 94/26878 | 11/1994 |
| WO | WO 94/28117 | 12/1994 |
| WO | WO 96/35442 | 11/1996 |
| WO | WO 97/14804 | 4/1997 |

OTHER PUBLICATIONS

*Bennet & Lasure, ed., *More Gene Manipulations in Fungi*, Academic Press, Inc. , pp. 70–76, 1991.
*Berges, Thierry et al., "Isolation of uridine auxotrophs from *Trichoderma reesei* and efficient transformation with the cloned ura3 and ura5 genes," *Current Genetics*, vol. 19, pp. 359–365, 1991.

*Cosgrove, Daniel et al., Autolysis and extension of isolated walls from growing cucumber hypocotyls, *Journal of Experimental Botany*, vol. 45, pp. 1711–1719, 1994.

*Cosgrove, Daniel J. Creeping walls, softening fruit, and penetration pollen tubes : The growing roles of expansins, >> *Proc. Natl. Acad. Sci. USA*, vol. 94, pp. 5504–5505 (1997).

*Fry, Stephen C., "Unzipped by expansins," *Current Biology*, vol. 4, No. 9, pp. 815–817, 1994.

*Keller, Elvira et al., "Expansins in growing tomato leaves," *The Plant Journal*, pp. 795–802, 1995.

*McQueen–Mason. Simon et al., "Two endogenous proteins that induce cell wall extension in plants," *The Plant Cell*, vol. 4, pp. 1425–1433, 1992.

*Sambrook, J. et al., ed. Molecular Cloning: A Laboratory Manual, 2nd ed. *Cold Spring Harbor Laboratory Press*, pp. 1.1–4.54 & 16.1–17.44, 1989.

*Shcherban, Tatyana Y. et al., Molecular cloning and sequence analysis of expansins—a highly conserved, multigene family of proteins that mediate cell wall extension in plants, *Proc., Natl. Acad. Sci. USA*, vol. 92, pp. 9245–9249, 1995.

*Sheir–Neiss, G. et al., "Characterization of the secreted cellulases of *Trichoderma reesei* wild type and mutants during controlled fermentations," *App. Microbiol. Biotechnol.* vol. 20, pp. 46–53, 1984.

*Wang, Ping et al., Production of expansin from light/dark growing *Trichosanthes kirilowii* var. *Japonicum* root cultures, *Biotechnology Letters*, vol. 16, No. 9, pp. 955–958, 1994.

*Ward, Michael et al., "Use of *Aspergillus* overproducing mutants, cured for integrated plasmid, to overproduce heterologous proteins," *Appl. Microbiol Biotechnol*, vol. 39, pp. 738–743, 1993.

*Zhen–Chang, Li et al., "An oat coleoptile wall protein that induces wall extension in vitro and that is antigenically related to a similar protein from cucumber hypocotyls," *Plants*, vol. 191, pp. 349–356, 1993.

*International Search Report of Jul. 9, 1998 for PCT/US 98/14226.

Primary Examiner—Jon Weber
Assistant Examiner—Rita Mitra
(74) Attorney, Agent, or Firm—Genencor International, Inc.

(57) ABSTRACT

A novel microbial protein is described which appears to have significant homology to plant expansin proteins and has the ability to weaken filter paper and swell cellulose. A DNA is described which encodes the novel protein.

14 Claims, 7 Drawing Sheets

```
GGCACGAGGAACTGTTAGACGGGATGGCTGGTAAGCTTATCCTCGTGGCTCTAGCAAGCCTTGTATCACTCTCTATTCAGCAGAATTGCG  90
                              M  A  G  K  L  I  L  V  A  L  A  S  L  V  S  L  S  I  Q  Q  N
                                                           ├──── signal sequence ────┤         ├─

CAGCATTATTGGCCAATGTGGAGGCATAGGGTGTCCGGCGGCACCATGTTGCTGTTGCTGGCCCAGTTTTGTCAATGACTGGT         180
 C  A  L  F  G  Q  C  G  G  I  G  W  S  G  T  T  C  C  V  A  G  Q  C  S  F  V  N  D  W
─┤                                ├──── CBD

ACTCCCAGTGCCTTGCGTCTTCACCCGGCGGCGGCGAAACCCCCAAACTGGCAGTGCTTCCACCTACACAACCACAGATACAGCTCCTCATT 270
 Y  S  Q  C  L  A  S  T  G  G  G  N  P  P  N  G  T  T  S  S  L  V  S  R  T  S  S  A  S  S

CCGTCGGCTCGTCTTCACCCGGTCGGCAGTGCTTCCACCTACACAACCACAGATACAGCTCCTCATT                           360
 S  V  G  S  S  P  G  G  N  S  P  T  G  S  A  S  T  Y  T  T  D  T  A  T  V  A  P  H

CGCAGTCTCCTTACCCCAGCATTGCCGCAGTTGCGGATCGTGGACCCTGTGTGGATAATGTTGCTGCCCATCATATTGTGCTAATG         450
 S  Q  S  P  Y  P  S  I  A  A  S  S  C  G  S  W  T  L  V  D  N  V  C  C  P  S  Y  C  A  N

ATGACACATCCGAGTCATGCTCAGGCTACCTGCGGTACTACAGAGAGCTGGACCGCCCCTCGGCCGAACATGCAAATCCGGAACTGCAAATCCGGAACTGTATCCAGAGAGTCC 540
 M  T  H  P  S  H  A  Q  A  T  C  G  T  T  E  S  W  T  R  P  A  A  E  H  A  N  P  E  L  Q  I  R  N  C  I  Q  R  V  P

GATCACGTATCCCAGCAACGAGAGCTGGACCACTTTGGCCTTAACGAGCGGCCTGTGTTTGGCTTAGCG                       630
 D  D  T  S  E  S  C  G  T  C  T  T  P  P  S  A  D  C  K  S  G  T  M  Y  P  E  V

CATCACGTATCCCAGCAACGAGAGCTGGACCACTTTGGCCTTAACGAGCGGCCTGTGTTTGGCTTAGCG                       720
 H  H  V  S  S  N  E  S  W  H  Y  S  R  S  T  H  F  G  L  T  S  G  G  A  C  G  F  G  L  Y

GTCTCTGCACAAAGGGCGACTAGTGTTACAGCCGGGACGTCAGCCTCCCAATTTGTTGTCCTGTTGCCAG                      810
 G  L  C  T  K  G  S  V  T  A  S  W  T  D  P  M  L  G  A  T  C  D  A  F  C  T  A  Y  P  L

TTTGCAAAGACCCTACCGGCACTACCCTCGTGGCAACTTCGCGGCAACTTCGCGGCAATGGCGATTACTACACACCCAATTCTGTCCTGTTGCCAG         900
 L  C  K  D  P  T  G  T  T  L  R  G  N  F  A  A  P  N  G  D  Y  Y  T  Q  F  W  S  S  L  P

GAGCCCTCGATAACTACCTGTCCGGCGAGTGCATTGAGCTGATACAAACAAAGCCCGATTATGCTGTCGGAGAAGCCG           900
 G  A  L  D  N  Y  L  S  G  E  C  I  E  L  I  Q  T  K  P  D  G  T  D  Y  A  V  G  E  A
```

FIG._1A

```
GCTACACGGATCCAATTACTCTCGAGATTGTGGACAGCTGCCCGTGCAGGCGCTGTGGTCCGGGCGCCGATCATT   990
 G  Y  T  D  P  I  T  L  E  I  V  D  S  C  P  C  S  A  N  S  K  W  C  C  G  P  G  A  D  H
GCGGAGAGATCGACTTCAAATACGGCTGTCCTCTCCTGCTGACAGCATTCATCTCGACTCGTCAGACATTGCCATGGCCGTTTGCAGG  1080
 C  G  E  I  D  F  K  Y  G  C  P  L  P  A  D  S  I  H  L  D  L  S  D  I  A  M  G  R  L  Q
GCAATGGATCACTAACCAATGGCGTCATCCCGACTCGATATAGAAGAGTCCCAAAGTTGGGAACGCCTACATTTGGCTTTCGAA  1170
 G  N  G  S  L  T  N  G  V  I  P  T  R  Y  R  R  V  Q  C  P  K  V  G  N  A  Y  I  W  L  R
ATGGCGGAGGGCCTTACTATTTGCTCTCACGGGCCAGTGCAACACGGACCGGCTCAGTCACCAAAATCGAGATCAAGGGCGCAGACA  1260
 N  G  G  G  P  Y  Y  F  A  L  T  A  V  N  T  N  G  P  G  S  V  T  K  I  E  I  K  G  A  D
CCGACAACTGGGTCGCTTGCCTTGGTCCATGACCCCAAACTATACGAGTAGCCGCCCACAAGAACGCTATGGCAGTTGGGTAATCCCACAGGGAT  1350
 T  D  N  W  V  A  L  V  H  D  P  N  Y  T  S  S  R  P  Q  E  R  Y  G  S  W  V  I  P  Q  G
CAGGGCCCTTAACTTGCCTGTTGGAATTCGTCTGACTAGCCCAACGGGGAACAGATTGTGAATGAACAGGCCATCAAGACATTCACTC  1440
 S  G  P  F  N  L  P  V  G  I  R  L  T  S  P  T  G  E  Q  I  V  N  E  Q  A  I  K  T  F  T
CTCCGGCCACAGGTGACCCCAATTTTTACTACAGACATTGGTGTGCAGTTTAGCCAGAATTGATGGCAAGCATTGGGCAATGGCTTC  1530
 P  P  A  T  G  D  D  P  N  F  Y  Y  I  D  I  G  V  Q  F  S  D  N  .  W  Q  A  L  G  N  G
TTGCTGTGGGACAATGATGTAGGCTAGATTCTCAAGTATGGTTCAAGTATGTGTACGTCTTCGTGTGTATAGATAGGTATGCTGTTCACT  1620
TAAATACACATCCTTTGGTACGTTG  1645
```

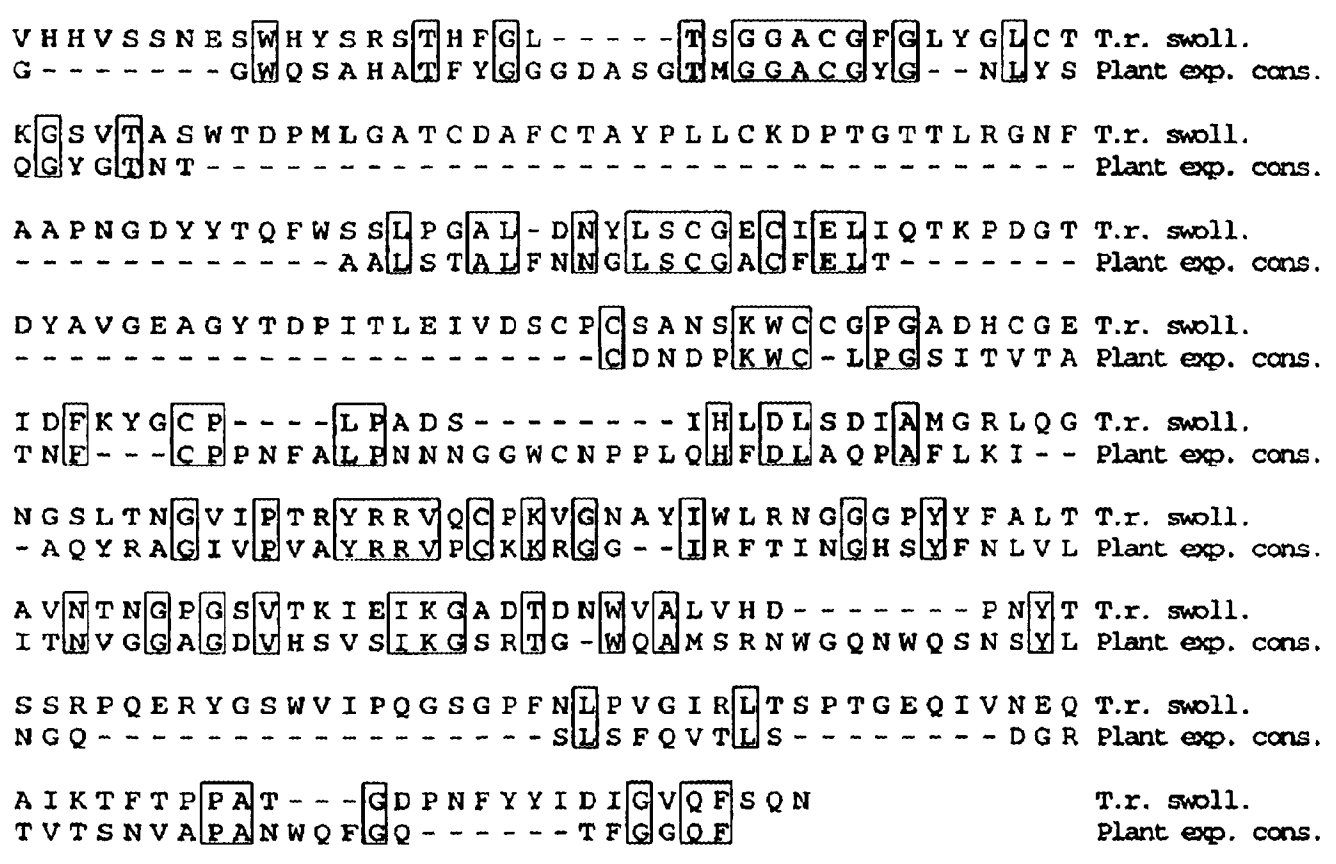

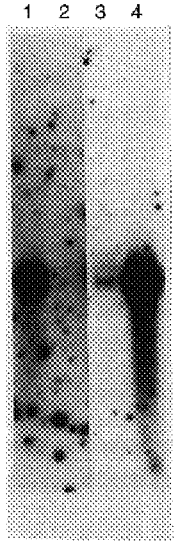
FIG._3
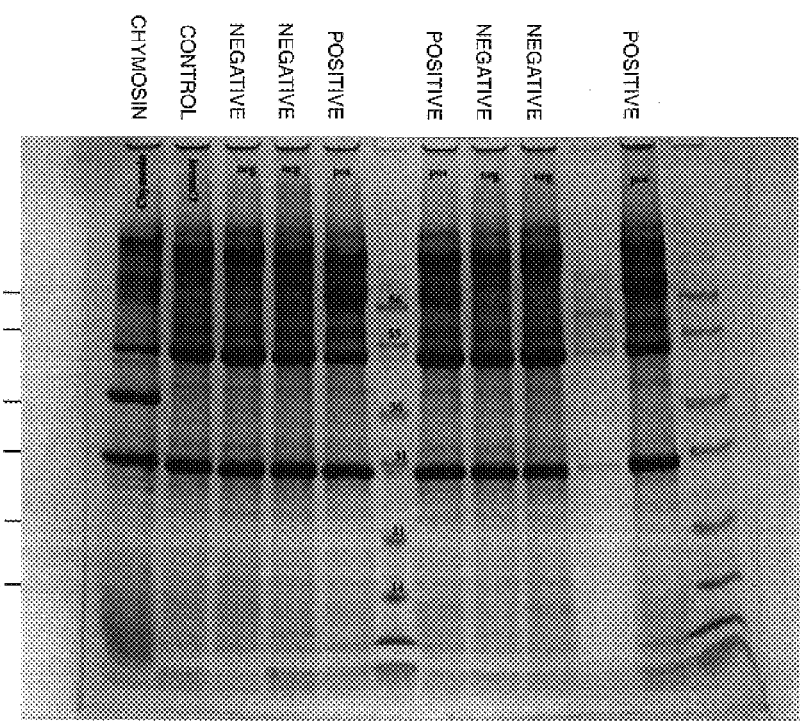
FIG._6

FIG. 4A

```
              160         170         180         190         200         210         220         230
         ....|....D....+....|.........w....|....w....+..w....|.........w....|........D..+....|.........w....|
consen.  VLITNVGGAGDV-hSVSiKGSrI-gWQaMSRNWGQNWQSNSYLnGQSLSFqVT1SDGRTvTSnNVAPanWqFGQTF---GgQF CuExS1   VLITNVGGAGDV-hSVSiKGSrI-gWQaMSRNWGQNWQSNNYLnGQgLSFqVT1SDGRT1TAyNLiVPsnWFGQTY--eGpQF
CuExS2   VLITNVGGAGDI-kSVSiKGSksssnWtpMSRNWGaNWQSNSYLnGQSNSFkVTtSDGQVqVfnNVVPssWrFGQTFa-skvQFs
AtEx1    VLITNVGGAGDV-hSAmvKGSrI-gWQaMSRNWGQNWQSNSYLnGQSLSFkVTtSDGQTiVSnNVAnagWsFGQTF-t-GaQLr
AtEx2    VLITNVGGAGDI-rAVS1KGSkIdqWQsMSRNWGQNWQSNTYLrGQSLSFqVTdSDGRTvSyDVvPhdWqFGQTF--eGgQF
AtEx5    VLVTNVGGAGDV-hSVSmKGSrI-kWQ1MSRNWGQNWQSNSYLnGQSLSFvVTtSDrRSvVSfNVAPptWsFGQTY-t-GgQFry
AtEx6    VLVTNVAGAGNI-vrlgvKGThI-sWmtMSRNWGQNWQSNSvLvGQSLSFrVTsSDrRSsTSwNIAPanWkFGQTF-m-GkNFrv
RiExB    VLVTNVAGPGDV-qSVSiKGSsI-gWQpMSRNWGQNWQSNSYLdGQSLSFqVavSDGRTvTSnNVVPagWqFxQTF--eGgQF
RiExD    VtVTNVGGSGvV-aqMSiKGSnI-gWmaMSRNWGaNWQSNaYLaGQSLSFiYQlDGRkvTAwNVAPsnWFGaTYstswvQF
Pea      VLITNVAGAGDI-vrYSvKGInI-aWmtMSRNWGQNWQSNavFvGQALSFrVTgSDrRTsTSwNVAPphWqFGQTF-t-GkNFrv
PhPl                G            W       WG W          G          EG T T       P W    Y
         L  V G GDV  Y IK      W                                                  Y
```

FIG._4B

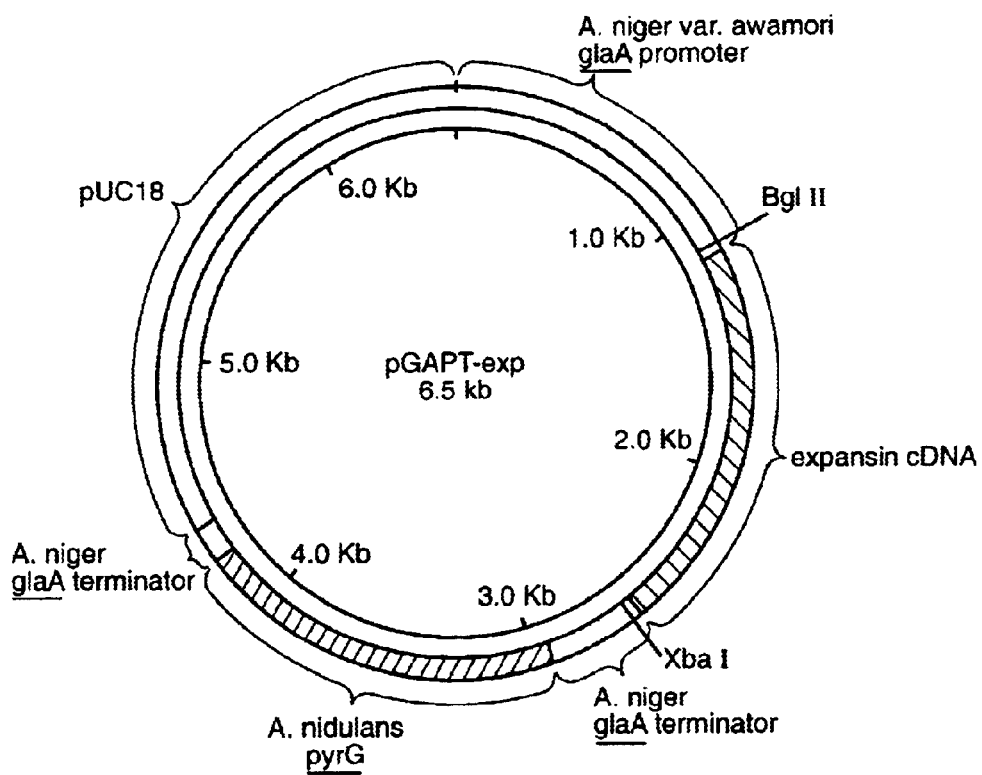
FIG._5

MICROBIAL SWOLLENIN PROTEIN, DNA SEQUENCES ENCODING SUCH SWOLLENINS AND METHOD OF PRODUCING SUCH SWOLLENINS

This application is a division of U.S. application Ser. No. 09/112,498 filed on Jul. 9, 1998, issued as U.S. Pat. No. 6,458,928, on Oct. 1, 2002, which is a continuation in part of U.S. application Ser. No. 08/893,766, filed on Jul. 11, 1997, now abandoned and which is incorporated herein by reference in its entirety.

BACKGROUND OF THE INVENTION

Osmotic uptake of water is the driving force of plant cell expansion. As water enters the cell, the protoplast expands but is restrained by the cell wall. Moreover, a rigid complex of cellulose microfibril polymers embedded in a glue-like matrix of pectins, hemicelluloses and proteins forms part of this wall in mature cells. It has long been thought that some "wall loosening" factor must be present which alters immature cell wall mechanical properties and allows it to undergo a process of elongation. McQueen-Mason et al., *Plant Cell*, Vol. 4, pp. 1425–1433 (1992) studied plant cell enlargement regulation by employing a reconstitution approach. The authors found that a crude protein extract from the cell walls of growing cucumber seedlings possess the ability to induce the extension of isolated cell walls. Sequential HPLC fractionation of the active wall extract revealed two proteins with molecular masses of 29 and 30 kD associated with the activity. Each protein, by itself, could induce wall extension without detectable hydrolytic breakdown of the wall and appeared to mediate "acid growth" responses of isolated walls and may catalyze plant cell wall extension by a novel biochemical mechanism.

Shcherban et al., *Proc. Nat. Acad. Sci.*, USA, Vol. 92, pp. 9245–9249 (1995) isolated cDNA's encoding these two cucumber proteins and compared them to anonymous expressed sequence tags from various sources. Rice and *Arabidopsis* expansin cDNA were identified from these collections and showed at least four different expansin cDNA's in rice and six different expansin cDNA's in *Arabidopsis*. The authors concluded that expansin are highly conserved in size and sequence (60–87% amino acid identity and 75–95% similarity between any pairwise comparison) and that the multigene family formed before the evolutionary divergence between monocotyledons and dicotyledons. Shcherban et al. states that the high conservation of this mutligene family indicates that the mechanism by which expansin promotes cell wall extension tolerates little variation in protein structure.

Wang et al., *Biotech. Lett.*, Vol. 16, No. 9, pp. 955–958 (1994) discovered two proteins in a Chinese medicinal cucumber, *Trichosanthes kirilowii*, which appear to be similar to the S1 and S2 proteins which demonstrate cell wall extension properties. Similar proteins were also found in growing tomato leaves (Keller et al., *The Plant Journal*, Vol. 8, No. 6, pp. 795–802 (1995)) and in oat coleoptile walls (Li et al., *Planta*, Vol. 191, pp. 349–356 (1993)).

Cosgrove et al., *J. Exp. Botany*, Vol. 45, Special Issue, pp.1711–1719 (1994) suggested that cooperative interactions between the expansin proteins and pectinases and cellulases may occur, wherein the enzymes modify the matrix so that other wall extension mechanisms may be more effective. Fry, *Current Biology*, Vol. 4, No. 9 (1994) suggest that, in loosening cell walls, expansin seems unlikely to break cellulose-cellulose bonds as microfibrils remain intact during growth. Thus, the authors discount the observed breakage of hydrogen bonds in filter paper as a side issue and suggest that expansin may lengthen inter-microfibrillar tethers by causing hemicellulose chains to detach from cellulose microfibrils to allow extension.

Despite the pioneering work previously done in the area of cell wall extension and its causes, work related to the usefulness and operability of expansins is still in its infancy. Moreover, the sources of expansin up to now have been exclusively from plant origins, for which expression systems may not be optimal for large scale production. Accordingly, it would be valuable to have a ready source of expansin-like material which is capable of being produce in large quantities from organisms which are established high output producers of biological materials, such as fungi, bacteria or other well characterized microorganisms.

SUMMARY OF THE INVENTION

It is an object of the present invention to provide for a swollenin protein which is derived from a microbial non-plant source.

It is another object of the present invention to provide for a swollenin protein which is expressible in a well-characterized microorganism, for example a fungus or bacteria, so as to facilitate its production in large quantities.

It is yet another object of the present invention to provide a DNA sequence corresponding to a microbial swollenin which can be used in industrial production of swollenin protein.

It is yet another object of the present invention to provide for novel and useful methods of altering cellulosic substrates, such as pulp and paper, cellulose based textile fibers, animal feed and corn wet milling or dry milling polysaccharide waste products or other cellulosic biomass.

According to the present invention, a partially or wholly isolated swollenin protein derived from a fungus or bacteria is provided. Preferably, the swollenin is derived from a filamentous fungus, more preferably, from a filamentous fungus such as *Trichoderma* spp., *Humicola* spp., *Neurospora* spp., *Aspergillus* spp., *Fusarium* spp., *Penicillium* spp., or *Gliocladium* spp. and most preferably, from *Trichoderma* spp. In a particularly preferred embodiment of the present invention, the swollenin comprises a sequence according to SEQ. ID NO:2, has at least 70% sequence identity with the sequence provided in SEQ. ID NO:2 or comprises a derivative of the sequence according to SEQ. ID NO:2, wherein the swollenin further has the ability to weaken filter paper and/or swell cotton fibers.

In another embodiment of the present invention, a DNA is provided encoding a swollenin protein from a fungus or bacteria. Preferably, the DNA is derived from a filamentous fungus such as *Trichoderma* spp., *Humicola* spp., *Neurospora* spp., *Aspergillus* spp., *Fusarium* spp., *Penicillium* spp., or *Gliocladium* spp. Also preferably, the DNA comprises the sequence according to SEQ. ID. NO:1. Alternately, the DNA has at least 70% sequence identity with the sequence according to SEQ. ID NO:1 or comprises a derivative of the sequence according to SEQ. ID NO:1, wherein said DNA encodes a swollenin protein which has the ability to weaken filter paper and/or swell cotton fibers. In a preferred embodiment of the invention, the DNA hybridizes with a DNA having all or part of the sequence provided in SEQ ID NO:1.

In another embodiment of the invention, a DNA is provided which encodes a microbial, e.g., bacterial or fungal, swollenin, and the DNA hybridizes with a DNA probe encoding a peptide having an amino acid sequence comprising SEQ. ID NO:14, SEQ. ID NO:15, SEQ. ID NO:16, SEQ. ID NO:17 SEQ. ID NO:18, SEQ ID NO: 33, SEQ ID NO: 34, SEQ ID NO: 36, SEQ ID NO: 37 or SEQ ID NO: 38. Vectors comprising such DNA, host cells having been transformed with such vectors and fermentation broths produced by such transformed host cells are also within the scope of the present invention.

In yet another embodiment of the present invention, a method of producing swollenin protein is provided comprising the steps of (a) obtaining a host cell which has been transformed with a vector comprising DNA encoding a swollenin protein, the DNA being isolated from a fungus or bacteria; (b) culturing the host cell under conditions suitable for the expression and, optionally, secretion, of the swollenin protein; and (c) recovering the fermentation broth containing said swollenin protein.

Since fungi and bacteria do not generally have a cellulosic cell wall and in any event are not known to increase in size by the same mechanism as higher plants, Applicants discovery that these microorganisms produce proteins having expansin-like properties is not suggested by previous work related to plant expansins. Thus, the finding that the cellulolytic fungus Trichoderma spp. produces an expansin-like protein is unexpected. However, it is apparent that the microbial class of proteins differs from those heretofore discovered in plants. For example, the presence of a region on the microbial swollenin protein described herein corresponding to the cellulose binding domain of fungal cellulolytic enzymes suggests that this protein is secreted to act in concert with the naturally secreted cellulases and hemicellulases in order to facilitate hydrolysis of cellulosic biomass in the environment. Consistent with this suggestion, the Trichoderma reesei swollenin gene was found to be expressed when the fungus was grown on cellulose as a sole carbon source, but not when the carbon source for growth was glucose. This pattern of regulation of gene expression is similar to that observed for many of the Trichoderma cellulose and hemicellulose genes. These unexpected findings lead to the conclusion that cellulose or hemicellulose degrading micro-organisms, including bacteria, yeast and fungi, would also produce such swollenin proteins.

Accordingly, it is an advantage of the present invention that the swollenins provided herein may have utility in many applications for which cellulase is currently used, for example, cleaning textiles (laundry detergents and pre-wash compositions), modifying textiles (depilling, color restoration, anti-greying), stonewashing denim, biomass conversion to glucose, and improvement of the nutritive value of animal feeds. Similarly, it is contemplated that an advantage of the present invention is that swollenins may have a synergistic or additive effect in combination with other enzymes, particularly cellulases such as endoglucanases. In other cases, it is possible that swollenins would have a deleterious effect in an application; for example, they may cause excessive fabric strength loss when present as a side activity in an endoglucanase produced by fermentation of a microorganism and used for fabric cleaning or modification. In such a case, removal of the swollenin from a cellulase product may be beneficial and may be accomplished by biochemically removing the product from the resultant cellulase mixture, through genetic engineering to prevent its expression or to inactivate the gene or by adding a chemical inhibitor to the composition comprising the swollenin.

BRIEF DESCRIPTION OF THE DRAWINGS

FIG. 1A–B illustrates the nucleotide sequence (SEQ ID NO:1) and predicted corresponding amino acid sequence (SEQ ID NO:2) of a cDNA clone obtained from a Trichoderma reesei (longibrachiatum) RNA after growth on a mixed carbon source.

FIG. 2 illustrates a comparison of the consensus amino acid sequence for plant expansin proteins (SEQ ID NO:3) and the sequence of the swollenin (SEQ ID NO:4) described herein showing the regions of amino acid homology.

FIG. 3 illustrates the result of Northern blotting of RNA samples prepared from Trichoderma reesei (longibrachiatum) mycelium grown on different carbon sources and probed with swollenin cDNA. Lane 1: cellulose; lane 2: glucose; lane 3: sorbitol; lane 4: sorbitol culture induced by sophorose.

FIG. 4A–B illustrates a comparison of nine known plant expansin amino acid sequences (SEQ ID NOS:5–15) showing the extensive homology present in plant expansins.

FIG. 5 shows the plasmid map for pGAPT-exp.

FIG. 6 illustrates the results of an SDS-PAGE gel run with culture supernatants and controls. Aspergillus transformants which were producing the T. reesei swollenin have a band running above the 66 kD marker band and this band is missing from lanes of the negative control (Aspergillus strain before the transformation).

DETAILED DESCRIPTION OF THE INVENTION

Definitions

"Swollenin" means a protein or polypeptide or domain of a protein or polypeptide of microbial, i.e., fungal or bacterial, origin which has the ability to facilitate weakening of filter paper and the swelling of cotton fibers without having cellulolytic activity, i.e., catalytic activity involving the breakage of individual cellulose strands into smaller monomer (glucose) or oligomers (polysaccharides). While it is useful to define swollenins loosely in terms of the expansin proteins described in McQueen-Mason et al., Plant Cell, Vol. 4, pp. 1425–1433 (1992), it is also apparent that microbial swollenins have distinct properties, for example, microbial swollenins are much larger proteins than plant expansins and have a low level of sequence identity with plant expansins. Moreover, certain microbial swollenin proteins exist in conjunction with a cellulose binding domain and may further exist in conjunction with a catalytic cellulase domain. For example, the swollenin protein derived from Trichoderma reesei shown herein possesses a cellulose binding domain.

It is contemplated herein that swollenins may be derived from microbial origins, and particularly from fungal or bacterial origins. Specifically, it is contemplated that microorganisms which possess cellulolytic capabilities will be excellent sources of swollenin protein. In a particularly preferred embodiment of the invention, the swollenin is derived from Trichoderma spp., particularly Trichoderma reesei (longibrachiatum). However, also preferably, the swollenin and/or DNA encoding swollenin according to the present invention is derived from a fungus, such as, Absidia spp.; Acremonium spp.; Agaricus spp.; Anaeromyces spp.; Aspergillus spp., including A. auculeatus, A. awamori, A. flavus, A. foetidus, A. fumaricus, A. fumigatus, A. nidulans, A. niger, A. oryzae, A. terreus and A. versicolor; Aeurobasidium spp.; Cephalosporum spp.; Chaetomium spp.; Coprinus spp.; Dactyllum spp.; Fusarium spp., including F. conglomerans, F. decemcellulare, F. javanicum, F. lini, F. oxysporum and F. solani; Gliocladium spp.; Humicola spp., including H. insolens and H. lanuginosa; Mucor spp.; Neurospora spp., including N. crassa and N. sitophila; Neocallimastix spp.; Orpinomyces spp.; Penicillium spp; Phanerochaete spp.; *Phlebia* spp.; *Piromyces* spp.; *Pseudomonas* spp.; *Rhizopus* spp.; *Schizophyllum* spp.; *Trametes* spp.; *Trichoderma* spp., including *T. reesei*, *T. reesei* (*longibrachiatum*) and *T. viride*; and *Zygorhynchus* spp. Similarly, it is envisioned that a swollenin and/or DNA encoding a swollenin as described herein may be found in cellulolytic bacteria such as *Bacillus* spp.; *Cellulomonas* spp.; *Clostridium* spp.; *Myceliophthora* spp.; *Thermomonospora* spp.; *Streptomyces* spp., including *S. olivochromogenes*; specifically fiber degrading ruminal bacteria such as *Fibrobacter succinogenes*; and in yeast including *Candida torresii; C. parapsilosis; C. sake; C. zeylanoides; Pichia minuta; Rhodotorula glutinis; R. mucilaginosa*; and *Sporobolomyces holsaticus*.

Preferably, swollenin proteins according to the present invention are isolated or purified. By purification or isolation is meant that the swollenin protein is altered from its natural state by virtue of separating the swollenin from some or all of the naturally occurring constituents with which it is associated in nature. This may be accomplished by art recognized separation techniques such as ion exchange chromatography, affinity chromatography, hydrophobic separation, dialysis, protease treatment, ammonium sulphate precipitation or other protein salt precipitation, centrifugation, size exclusion chromatography, filtration, microfiltration, gel electrophoresis or separation on a gradient to remove whole cells, cell debris, impurities, extraneous proteins, or enzymes undesired in the final composition. It is further possible to then add constituents to the swollenin containing composition which provide additional benefits, for example, activating agents, anti-inhibition agents, desirable ions, compounds to control pH or other enzymes such as cellulase.

Hybridization is used herein to analyze whether a given fragment or gene corresponds to the swollenin described herein and thus falls within the scope of the present invention. The hybridization assay is essentially as follows: Genomic DNA from a particular target source is fragmented by digestion with a restriction enzyme(s), e.g., EcoR I, Hind III, Bam HI, Cla I, Kpn I, Mlu I, Spe I, Bgl II, Nco I, Xba I, Xho I and Xma I (supplied by New England Biolabs, Inc., Beverly, Mass. and Boehringer Mannheim) according to the manufacturer's instructions. The samples are then electrophoresed through an agarose gel (such as, for example, 0.7% agarose) so that separation of DNA fragments can be visualized by size. The gel may be briefly rinsed in distilled $H_2O$ and subsequently depurinated in an appropriate solution (such as, for example, 0.25M HCl) with gentle shaking followed by denaturation for 30 minutes (in, for example, 0.4 M NaOH). A renaturation step may be included in which the gel is placed in 1.5 M NaCl, IM Tris, pH 7.0 with gentle shaking for 30 minutes. The DNA should then be transferred onto an appropriate positively charged membrane, for example the Maximum Strength Nytran Plus membrane (Schleicher & Schuell, Keene, N.H.), using a transfer solution (such as, for example, 6×SSC (900 mM NaCl, 90 mM trisodium citrate). After the transfer is complete, generally at about 2 hours or greater, the membrane is rinsed and air dried at room temperature after using a rinse solution (such as, for example, 2×SSC[2×SSC=300 mM NaCl, 30 mM trisodium citrate]). The DNA should then be crosslinked to the membrane by either UV-crosslinking or by baking in an oven using temperatures recommended by the membrane manufacturer. The membrane should then be prehybridized, (for approximately 2 hours or more) in a suitable prehybridization solution (such as, for example, an aqueous solution containing per 100 mls: 30–50 mls formamide, 25 mls of 20×SSPE (1×SSPE=0.18 M NaCl, 1 mM EDTA, 10 mM $NaH_2PO_4$, pH 7.7), 2.5 mls of 20% SDS, 1 ml of 10 mg/ml sheared herring sperm DNA).

A DNA probe taken from the sequence in FIG. 1 should be isolated by electrophoresis in an agarose gel, the fragment excised from the gel and recovered from the excised agarose. This purified fragment of DNA is then labeled (using, for example, the Megaprime labeling system according to the instructions of the manufacturer to incorporate $P^{32}$ in the DNA (Amersham International plc, Buckinghamshire, England)). The labeled probe is denatured by heating to 95° C. for 5 minutes and immediately added to the prehybridization solution above containing the membrane. The hybridization reaction should proceed for an appropriate time and under appropriate conditions, for example, for 18 hours at 37° C. with gentle shaking. The membrane is rinsed (for example, in 2×SSC/0.3% SDS) and then washed with an appropriate wash solution and with gentle agitation. The stringency desired will be a reflection of the conditions under which the membrane (filter) is washed.

Specifically, the stringency of a given reaction (i.e., the degree of homology necessary for successful hybridization) will depend on the washing conditions to which the filter from the Southern Blot is subjected after hybridization. "Low-stringency" conditions as defined herein will comprise washing a filter from a Southern Blot with a solution of 0.2×SSC/0.1% SDS at 20° C. for 15 minutes. "Standard-stringency" conditions comprise a further washing step comprising washing the filter from the Southern Blot a second time with a solution of 0.2×SSC/0.1% SDS at 37° C. for 30 minutes.

"Cellulase" is a well classified category of enzymes in the art and includes enzymes capable of hydrolyzing cellulose polymers to shorter oligomers and/or glucose. Common examples of cellulase enzymes include exo-cellobiohydrolases and endoglucanases and are obtainable from many species of cellulolytic organisms, particularly including fungi and bacteria.

"Hemicellulase" is also a well classified category of enzymes in the art and includes enzyme capable of hydrolyzing hemicellulose polymers to shorter oligomers. Common examples of hemicellulases include xylanase and mannanase.

"Cellulose containing materials" means materials comprising cellulose polymer as one of its constituents. Cellulose will thus include sewn or unsewn fabrics or other articles made of pure cotton or cotton blends including cotton woven fabrics, cotton knits, cotton denims, cotton yarns and the like or blends thereof including one or more non-cotton fibers including synthetic fibers such as polyamide fibers (for example, nylon 6 and nylon 66), acrylic fibers (for example, polyacrylonitrile fibers), and polyester fibers (for example, polyethylene terephthalate), polyvinyl alcohol fibers (for example, Vinylon), polyvinyl chloride fibers, polyvinylidene chloride fibers, polyurethane fibers, polyurea fibers and aramid fibers. "Cellulose" further means any cotton or non-cotton containing cellulosic fabric or cotton or non-cotton containing cellulose blend including natural cellulosics and manmade cellulosics (such as jute, flax, ramie, rayon, TENCEL®). Included under the heading of manmade cellulosics are regenerated fabrics that are well known in the art such as rayon. Other manmade cellulosics include chemically modified cellulose fibers (e.g, cellulose derivatized by acetate) and solvent-spun cellulose fibers. Of course, included within the definition of cellulose containing fabric is any garment or yarn made of such materials.

Similarly, "cellulose containing fabric" includes textile fibers made of such materials. Additionally, materials comprising cellulose include wood, wood pulp and other plant-based fiber (i.e., grasses, feeds, seeds, trees, corn husks), paper, cardboard, particle board, nutritional fiber and non-nutritional fiber.

"Derivative" means a protein which is derived from a precursor protein (e.g., the native protein) by addition of one or more amino acids to either or both the C- and N-terminal end, substitution of one or more amino acids at one or a number of different sites in the amino acid sequence, deletion of one or more amino acids at either or both ends of the protein or at one or more sites in the amino acid sequence, or insertion of one or more amino acids at one or more sites in the amino acid sequence. The preparation of a swollenin derivative is preferably achieved by modifying a DNA sequence which encodes for the native protein, transformation of that DNA sequence into a suitable host, and expression of the modified DNA sequence to form the derivative swollenin. The derivative of the invention includes peptides comprising altered amino acid sequences in comparison with a precursor amino acid sequence (e.g., a wild type or native state swollenin), which peptides retain a characteristic swollenin nature of the precursor swollenin but which have altered properties in some specific aspect. For example, a swollenin derivative may have an increased pH optimum or increased temperature or oxidative stability but will retain its characteristic cellulose modification activity. Similarly, derivatives according to the present invention include a cellulose binding domain which has either been added, removed or modified in such a way so as to significantly impair or enhance its cellulose binding ability. Similarly, a catalytic cellulolytic domain may either be added, removed or modified to operate in conjunction with the swollenin. It is contemplated that derivatives according to the present invention may be derived from a DNA fragment encoding a swollenin derivative wherein the functional activity of the expressed swollenin derivative is retained. Derivative further includes chemical modification to change the characteristics of the swollenin.

"Expression vector" means a DNA construct comprising a DNA sequence which is operably linked to a suitable control sequence capable of effecting the expression of the DNA in a suitable host. Such control sequences may include a promoter to effect transcription, an optional operator sequence to control transcription, a sequence encoding suitable ribosome-binding sites on the mRNA, and sequences which control termination of transcription and translation. Different cell types are preferably used with different expression vectors. A preferred promoter for vectors used in *Bacillus subtilis* is the AprE promoter; a preferred promoter used in *E. coli* is the Lac promoter, a preferred promoter used in *Saccharomyces cerevisiae* is PGK1, a preferred promoter used in *Aspergillus niger* is glaA, and a preferred promoter for *Trichoderma reesei* (longibrachiatum) is cbhI. The vector may be a plasmid, a phage particle, or simply a potential genomic insert. Once transformed into a suitable host, the vector may replicate and function independently of the host genome, or may, under suitable conditions, integrate into the genome itself. In the present specification, plasmid and vector are sometimes used interchangeably. However, the invention is intended to include other forms of expression vectors which serve equivalent functions and which are, or become, known in the art. Thus, a wide variety of host/expression vector combinations may be employed in expressing the DNA sequences of this invention. Useful expression vectors, for example, may consist of segments of chromosomal, non-chromosomal and synthetic DNA sequences such as various known derivatives of SV40 and known bacterial plasmids, e.g., plasmids from *E. coli* including col E1, pCR1, pBR322, pMb9, pUC 19 and their derivatives, wider host range plasmids, e.g., RP4, phage DNAs e.g., the numerous derivatives of phage λ, e.g., NM989, and other DNA phages, e.g., M13 and filamentous single stranded DNA phages, yeast plasmids such as the 2μ plasmid or derivatives thereof, vectors useful in eukaryotic cells, such as vectors useful in animal cells and vectors derived from combinations of plasmids and phage DNAs, such as plasmids which have been modified to employ phage DNA or other expression control sequences. Expression techniques using the expression vectors of the present invention are known in the art and are described generally in, for example, Sambrook et al., *Molecular Cloning: A Laboratory Manual, Second Edition*, Cold Spring Harbor Press (1989). Often, such expression vectors including the DNA sequences of the invention are transformed into a unicellular host by direct insertion into the genome of a particular species through an integration event (see e.g., Bennett & Lasure, *More Gene Manipulations in Fungi*, Academic Press, San Diego, pp. 70–76 (1991) and articles cited therein describing targeted genomic insertion in fungal hosts, incorporated herein by reference).

"Host strain" or "host cell" means a suitable host for an expression vector comprising DNA according to the present invention. Host cells useful in the present invention are generally procaryotic or eucaryotic hosts, including any transformable microorganism in which expression can be achieved. Specifically, host strains may be *Bacillus subtilis, Escherichia coli, Trichoderma reesei* (*longibrachiatum*), *Saccharomyces cerevisiae* or *Aspergillus niger*. Host cells are transformed or transfected with vectors constructed using recombinant DNA techniques. Such transformed host cells are capable of both replicating vectors encoding swollenin and its variants (mutants) or expressing the desired peptide product. In a preferred embodiment according to the present invention, "host cell" means both the cells and protoplasts created from the cells of *Trichoderma* sp.

"Signal sequence" means a sequence of amino acids bound to the N-terminal portion of a protein which facilitates the secretion of the mature form of the protein outside of the cell. This definition of a signal sequence is a functional one. The mature form of the extracellular protein lacks the signal sequence which is cleaved off during the secretion process.

"DNA construct or vector" (used interchangeably herein) means a nucleotide sequence which comprises one or more DNA fragments or DNA variant fragments encoding any of the novel swollenins or derivatives described above.

"Functionally attached to" means that a regulatory region, such as a promoter, terminator, secretion signal or enhancer region is attached to a structural gene and controls the expression of that gene.

Preparation of Swollenin

The present invention relates to the expression, purification and/or isolation and use of swollenins and derivatives of swollenins. These swollenins are preferably prepared by recombinant methods. However, swollenin proteins for use in the present invention may be obtained by other art recognized means such as purification from natural isolates.

A preferred mode for preparing swollenin according to the present invention comprises transforming a *Trichoderma* sp. host cell with a DNA construct comprising at least a fragment of DNA encoding a portion or all of the swollenin functionally attached to a promoter. The transformed host cell is then grown under conditions so as to express the desired protein. Subsequently, the desired protein product is purified to substantial homogeneity.

Preferably, the microorganism to be transformed comprises a strain derived from *Trichoderma* spp. or *Aspergillus* spp. More preferably, the strain comprises *T. reesei* (*longibrachiatum*) which is useful for obtaining overexpressed protein or *Aspergillus niger* var. *awamori*. For example, RL-P37, described by Sheir-Neiss et al. in *Appl. Microbiol. Biotechnology*, 20 (1984) pp. 46–53 is known to secrete elevated amounts of cellulase enzymes. Functional equivalents of RL-P37 include *Trichoderma reesei* (*longibrachiatum*) strain RUT-C30 (ATCC No. 56765) and strain QM9414 (ATCC No. 26921). Another example includes overproducing mutants as described in Ward et al. in *Appl. Microbiol. Biotechnology* 39:738–743 (1993). It is contemplated that these strains would also be useful in overexpressing *Trichoderm* spp. swollenin.

Where it is desired to obtain the swollenin protein in the absence of cellulolytic activity, it is useful to obtain, for example, a *Trichoderma* host cell strain which has had one or more cellulase genes deleted prior to introduction of a DNA construct or plasmid containing the DNA fragment encoding the swollenin. Such strains may be prepared by the method disclosed in U.S. Pat. No. 5,246,853 and WO 92/06209, which disclosures are hereby incorporated by reference. By expressing a swollenin in a host microorganism that is missing one or more cellulase genes, the identification and subsequent purification procedures are simplified. Any gene from *Trichoderma* sp. which has been cloned can be deleted, for example, the cbh1, cbh2, egl1, and egl3 genes as well as those encoding EGIII and/or EGV protein (see e.g., U.S. Pat. No. 5,475,101 and WO 94/28117, respectively).

Gene deletion may be accomplished by inserting a form of the desired gene to be deleted or disrupted into a plasmid by methods known in the art. The deletion plasmid is then cut at an appropriate restriction enzyme site(s), internal to the desired gene coding region, and the gene coding sequence or part thereof replaced with a selectable marker. Flanking DNA sequences from the locus of the gene to be deleted or disrupted, preferably between about 0.5 to 2.0 kb, remain on either side of the selectable marker gene. An appropriate deletion plasmid will generally have unique restriction enzyme sites present therein to enable the fragment containing the deleted gene, including flanking DNA sequences, and the selectable marker gene to be removed as a single linear piece.

A selectable marker must be chosen so as to enable detection of the transformed fungus. Any selectable marker gene which is expressed in the selected microorganism will be suitable. For example, with *Trichoderma* sp., the selectable marker is chosen so that the presence of the selectable marker in the transformants will not significantly affect the properties thereof. Such a selectable marker may be a gene which encodes an assayable product. For example, a functional copy of a *Trichoderma* sp. gene may be used which if lacking in the host strain results in the host strain displaying an auxotrophic phenotype.

In a preferred embodiment, a pyr4⁻ derivative strain of *Trichoderma* sp. is transformed with a functional pyr4 gene, which thus provides a selectable marker for transformation. A pyr4⁻ derivative strain may be obtained by selection of *Trichoderma* sp. strains which are resistant to fluoroorotic acid (FOA). The pyr4 gene encodes orotidine-5'-monophosphate decarboxylase, an enzyme required for the biosynthesis of uridine. Strains with an intact pyr4 gene grow in a medium lacking uridine but are sensitive to fluoroorotic acid. It is possible to select pyr4⁻ derivative strains which lack a functional orotidine monophosphate decarboxylase enzyme and require uridine for growth by selecting for FOA resistance. Using the FOA selection technique it is also possible to obtain uridine requiring strains which lack a functional orotate pyrophosphoribosyl transferase. It is possible to transform these cells with a functional copy of the gene encoding this enzyme (Berges and Barreau, 1991, *Curr. Genet.* 19 pp. 359–365). Selection of derivative strains is easily performed using the FOA resistance technique referred to above, and thus, the pyr4 gene is preferably employed as a selectable marker.

To transform pyr4⁻ *Trichoderma* sp. so as to be lacking in the ability to express one or more cellulase genes, a single DNA fragment comprising a disrupted or deleted cellulase gene is then isolated from the deletion plasmid and used to transform an appropriate pyr⁻ *Trichoderma* host. Transformants are then identified and selected based on their ability to express the pyr4 gene product and thus compliment the uridine auxotrophy of the host strain. Southern blot analysis is then carried out on the resultant transformants to identify and confirm a double crossover integration event which replaces part or all of the coding region of the genomic copy of the gene to be deleted with the pyr4 selectable markers.

Although the specific plasmid vectors described above relate to preparation of pyr⁻ transformants, the present invention is not limited to these vectors. Various genes can be deleted and replaced in the *Trichoderma* sp. strain using the above techniques. In addition, any available selectable markers can be used, as discussed above. In fact, any *Trichoderma* sp. gene which has been cloned, and thus identified, can be deleted from the genome using the above-described strategy.

As stated above, the host strains used are derivatives of *Trichoderma* sp. which lack or have a nonfunctional gene or genes corresponding to the selectable marker chosen. For example, if the selectable marker of pyr4 is chosen, then a specific pyr4⁻ derivative strain is used as a recipient in the transformation procedure. Similarly, selectable markers comprising *Trichoderma* sp. genes equivalent to the *Aspergillus nidulans* genes amdS, argB, trpC, niaD may be used. The corresponding recipient strain must therefore be a derivative strain such as argB⁻, trpc⁻, niaD⁻, respectively.

DNA encoding the swollenin protein is then prepared for insertion into an appropriate microorganism. According to the present invention, DNA encoding for a swollenin enzyme comprises all of the DNA necessary to encode for a protein which has functional swollenin activity. Accordingly, DNA may be derived from any microbial source which produces swollenin, provided that the gene may be identified and isolated pursuant to the methods described herein. In a preferred embodiment, the DNA encodes for an swollenin protein derived from *Trichoderma* sp., and more preferably from *Trichoderma reesei* (*longibrachiatum*).

The DNA fragment or DNA variant fragment encoding the swollenin or derivative may be functionally attached to a fungal promoter sequence, for example, the promoter of the cbh1 or egl1 gene.

It is also contemplated that more than one copy of DNA encoding a swollenin may be recombined into the strain to facilitate overexpression.

The DNA encoding the swollenin may be prepared by the construction of an expression vector carrying the DNA encoding the truncated cellulase. The expression vector carrying the inserted DNA fragment encoding the swollenin may be any vector which is capable of replicating autonomously in a given host organism or of integrating into the DNA of the host, typically a plasmid. In preferred embodiments two types of expression vectors for obtaining expression of genes are contemplated. The first contains DNA sequences in which the promoter, gene coding region, and terminator sequence all originate from the gene to be expressed. Gene truncation may be obtained by deleting away undesired DNA sequences (e.g., coding for unwanted domains) to leave the domain to be expressed under control of its own transcriptional and translational regulatory sequences. A selectable marker is also contained on the vector allowing the selection for integration into the host of multiple copies of the novel gene sequences.

The second type of expression vector is preassembled and contains sequences required for high level transcription and a selectable marker. It is contemplated that the coding region for a gene or part thereof can be inserted into this general purpose expression vector such that it is under the transcriptional control of the expression cassettes promoter and terminator sequences. For example, pTEX is such a general purpose expression vector. Genes or part thereof can be inserted downstream of the strong cbhl promoter.

In the vector, the DNA sequence encoding the swollenin of the present invention should be operably linked to transcriptional and translational sequences, i.e., a suitable promoter sequence and signal sequence in reading frame to the structural gene. The promoter may be any DNA sequence which shows transcriptional activity in the host cell and may be derived from genes encoding proteins either homologous or heterologous to the host cell. The signal peptide provides for extracellular production of the swollenin or derivatives thereof. The DNA encoding the signal sequence is preferably that which is naturally associated with the gene to be expressed, however the signal sequence from any suitable source, for example an exo-cellobiohydrolases or endoglucanase from *Trichoderma*, is contemplated in the present invention.

The procedures used to ligate the DNA sequences coding for the swollenins of the present invention with the promoter, and insertion into suitable vectors are well known in the art.

The DNA vector or construct described above may be introduced in the host cell in accordance with known techniques such as transformation, transfection, microinjection, microporation, biolistic bombardment and the like.

In the preferred transformation technique, it must be taken into account that the permeability of the cell wall to DNA in *Trichoderma* sp. is very low. Accordingly, uptake of the desired DNA sequence, gene or gene fragment is at best minimal. There are a number of methods to increase the permeability of the *Trichoderma* sp. cell wall in the derivative strain (i.e., lacking a functional gene corresponding to the used selectable marker) prior to the transformation process.

The preferred method in the present invention to prepare *Trichoderma* sp. for transformation involves the preparation of protoplasts from fungal mycelium. The mycelium can be obtained from germinated vegetative spores. The mycelium is treated with an enzyme which digests the cell wall resulting in protoplasts. The protoplasts are then protected by the presence of an osmotic stabilizer in the suspending medium. These stabilizers include sorbitol, mannitol, potassium chloride, magnesium sulfate and the like. Usually the concentration of these stabilizers varies between 0.8 M to 1.2 M. It is preferable to use about a 1.2 M solution of sorbitol in the suspension medium.

Uptake of the DNA into the host *Trichoderma* sp. strain is dependent upon the calcium ion concentration. Generally between about 10 mM $CaCl_2$ and 50 mM $CaCl_2$ is used in an uptake solution. Besides the need for the calcium ion in the uptake solution, other items generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG). It is believed that the polyethylene glycol acts to fuse the cell membranes thus permitting the contents of the medium to be delivered into the cytoplasm of the *Trichoderma* sp. strain and the plasmid DNA is transferred to the nucleus. This fusion frequently leaves multiple copies of the plasmid DNA tandemly integrated into the host chromosome.

Usually a suspension containing the *Trichoderma* sp. protoplasts or cells that have been subjected to a permeability treatment at a density of $10^8$ to $10^9$/ml, preferably $2 \times 10^8$/ml are used in transformation. A volume of 100 microliters of these protoplasts or cells in an appropriate solution (e.g., 1.2 M sorbitol; 50 mM $CaCl_2$) are mixed with the desired DNA. Generally a high concentration of PEG is added to the uptake solution. From 0.1 to 1 volume of 25% PEG 4000 can be added to the protoplast suspension. However, it is preferable to add about 0.25 volumes to the protoplast suspension. Additives such as dimethyl sulfoxide, heparin, spermidine, potassium chloride and the like may also be added to the uptake solution and aid in transformation.

Generally, the mixture is then incubated at approximately 0° C. for a period of between 10 to 30 minutes. Additional PEG is then added to the mixture to further enhance the uptake of the desired gene or DNA sequence. The 25% PEG 4000 is generally added in volumes of 5 to 15 times the volume of the transformation mixture; however, greater and lesser volumes may be suitable. The 25% PEG 4000 is preferably about 10 times the volume of the transformation mixture. After the PEG is added, the transformation mixture is then incubated at room temperature before the addition of a sorbitol and $CaCl_2$ solution. The protoplast suspension is then further added to molten aliquots of a growth medium. This growth medium permits the growth of transformants only. Any growth medium can be used in the present invention that is suitable to grow the desired transformants. However, if Pyr+ transformants are being selected it is preferable to use a growth medium that contains no uridine. The subsequent colonies are transferred and purified on a growth medium depleted of uridine.

At this stage, stable transformants may be distinguished from unstable transformants by their faster growth rate and the formation of circular colonies with a smooth, rather than ragged outline on solid culture medium lacking uridine. Additionally, in some cases a further test of stability may made by growing the transformants on solid non-selective medium (i.e. containing uridine), harvesting spores from this culture medium and determining the percentage of these spores which will subsequently germinate and grow on selective medium lacking uridine.

In a particular embodiment of the above method, the swollenins or derivatives thereof are recovered in active form from the host cell after growth in liquid media either as a result of the appropriate post translational processing of the novel swollenin or derivatives thereof.

The expressed swollenins are recovered from the medium by conventional techniques including separations of the cells from the medium by centrifugation, filtration, and precipitation of the proteins in the supernatant or filtrate with a salt, for example, ammonium sulphate. Additionally, chromatography procedures such as ion exchange chromatography or affinity chromatography may be used. Antibodies (polyclonal or monoclonal) may be raised against the natural purified swollenins, or synthetic peptides may be prepared from portions of the swollenin molecule and used to raise polyclonal antibodies.

EXAMPLE 1

*Trichoderma reesei (longibrachiatum)* cDNA Clone Encoding a Novel Swollenin

FIG. 1 shows the nucleotide sequence (SEQ ID:NO 1) and predicted corresponding amino acid sequence (SEQ ID:NO 2) of a cDNA clone obtained from a library of cDNA prepared from *Trichoderma reesei (longibrachiatum)* RNA after growth on a mixed carbon source as described by Saloheimo et al. 1994, Molec. Microbiol. 13:219–228. The cDNA showed the following characteristics which help to describe the gene:

An open reading frame of 1482 nt was identified and the encoded protein was deduced.

The first 18 amino acids of the predicted protein have the following features expected of a secretion signal sequence and signal cleavage site. There is a positively charged amino acid (lysine) close to the amino-terminal methionine which is followed by a sequence of hydrophobic amino acids and an apparent signal peptidase cleavage site following amino acid Ile18. The predicted N-terminus of the mature swollenin would therefore be Gln-Gln. Similarly, many of the mature cellulases produced by *Trichoderma* have glutamine at the N-terminus (e.g., CBHI, CBHII, EGI, EGII and EGIII) and both EGI and EGII begin with a pair of glutamine residues reinforcing the conclusion that this is the N-terminus. The mature protein is therefore predicted to be 475 amino acids in length and have a molecular weight of approximately 49.5 kDa, not including any possible glycosylation or other modification, and a calculated pI of approximately 4.6 based on the amino acid composition. There are three potential N-linked glycosylation sites (having the consensus amino acid sequence of N-X-S/T) at Asparagines 160, 336 and 406.

Residues 4 to 39 of the predicted mature protein sequence have close similarity with the cellulose binding domains (CBDs) of cellulases produced by *Trichoderma* and other fungal cellulases (58% identity with the CBD of CBHII of *Trichoderma*). CBDs are also associated with some non-cellulolytic extracellular fungal enzymes such as acetyl xylan esterase and mannanase from *Trichoderma reesei (longibrachiatum)* and similar identity is shown between swollenin CBD and these CBD's.

Following the CBD of the predicted *Trichoderma* protein is a region (from residue 41 to approximately residue 86) which is rich in Ser, Thr, Gly and Pro residues and which should share a similar functionality to the linker or hinge regions present in *Trichoderma* and other fungal cellulases and which connect the CBD with the catalytic domain.

Regions of similarity are observed between the predicted amino acid sequence (SEQ ID NO: 2) of the *Trichoderma* swollenin of FIG. 1 and known sequences of higher plant expansins. FIG. 2 shows an alignment between part of the predicted *Trichoderma* protein and a consensus sequence (SEQ ID NO: 3) derived from nine plant expansins by Shcherban et al., supra. These sequences were aligned using the Jotun Hein algorithm within the Lasergene software package (DNASTAR Inc.) and a 36% similarity was calculated between the two amino acid sequences. Of the 322 amino acids of *Trichoderma* swollenin sequence used in this alignment, 70 or 21.7% are identical to the higher plant consensus sequence.

Regions of similarity can also be observed between the *Trichoderma reesei (longibrachiatum)* swollenin and human titin protein that is rich in fibronectin type repeats. The homology was detected in a similarity search to the protein sequence databanks carried out with the program BLAST (Altschul et al., 1990, *J. Mol. Biol.* 215:403–410) and the alignments shown as examples have been created by the program. The regions of titin homologous to the *T. reesei* swollenin are parts of the fibronectin type repeats. Fibronectin repeats have been found in some bacterial carbohydrate-modifying enzymes (Little et al., 1994, *J. Mol. Evol.* 39:631–643) but not from any fungal protein. A BLAST search reveals no similarity between the plant expansins and fibronectin repeat containing proteins.

|  |  |  |
|---|---|---|
| T.r.swo | 283 | GGPYYFALTAVNTNGPGSVTKI (SEQ. ID NO:21) |
| Human titin | 12268 | GNEYYFRVTAVNEYGPGVPTDV (SEQ. ID NO:22) |
| T.r.swo | 100 | TKGSVTASWTDPMETLGA (SEQ. ID NO:23) |
| Human titin | 9114 | TKGSMLVSWTPPLDNGGS (SEQ. ID NO:24) |

The *Trichoderma reesei (longibrachiatum)* swollenin gene was expressed when the fungus was grown on cellulose as the sole carbon source, but not when grown on glucose as the sole carbon source.

In order to investigate the regulation of swollenin gene expression in *Trichoderma* the following experiment was performed. *Trichoderma reesei (longibrachiatum)* strain QM9414 was grown in shake flasks (28° C., 200 RPM) in a minimal medium (Penttilä et al., 1987, *Gene* 61:155–164) containing 5% glucose or 2% cellulose for three days. To test for sophorose induction, the strain was grown in a minimal medium with 2% sorbitol for three days and sophorose was added to the final concentration of 1 mM. The culture was continued for another ten hours and the same amount of sophorose was added. The cultivation was ended five hours after the second addition. A 87 h cultivation in 2% sorbitol was carried out without sophorose additions as a control. After the cultivations the mycelium was harvested by filtration with a glass fibre filter, washed with 0.9% NaCl and frozen. Total RNA was isolated from the mycelial samples according to Chirgwin et al. (1979, *Biochem. J.* 18:5294–5299). RNA samples of 5 μg were treated with glyoxal and run in a 1% agarose gel in 10 mM Na-phosphate buffer, pH 7. Capillary blotting onto a Hybond-N nylon membrane,(Amersham) was carried out according to manufacturer's instructions. The hybridization probe was prepared by digesting the cDNA library plasmid carrying the swollenin cDNA with EcoRI and XhoI, running the digested plasmid in a 0.8% agarose gel and isolating the cDNA fragment from the gel with the Qiaquick gel extraction kit (Qiagen). The probe was labelled with $^{32}$P-dCTP using the Random Primed DNA labelling kit (Boehringer Mannheim). Hybridization was one for 24 h at 42° C. in 50% formamide, 10% dextran sulphate, 1% SDS, 1M NaCl, 125 μg/ml herring sperm DNA. The filter was washed at 42° C. in 5×SSPE for 15 minutes, in 1×SSPE, 0.1% SDS for 2×15 minutes and in 0.1×SSPE, 0.1% SDS 2×15 minutes at room temperature. (1×SSPE is 0.18 M NaCl, 1 mM EDTA, 10 mM $NaH_2PO_4$, pH 7.7). The results of this experiment are shown in FIG. 3. No swollenin mRNA was observed after growth on glucose and very little was observed after growth on sorbitol. In contrast, high levels of swollenin mRNA were observed after growth on cellulose or after addition of sophorose to a sorbitol-grown culture.

EXAMPLE 2

Preparation Of A Cloned DNA Molecule Encoding Trichoderma Swollenin

The following is provided as a method of preparing a clone comprising an entire swollenin gene described in Example 2. In this example, genomic DNA or cDNA clones derived from Trichoderma and are prepared by using the following procedure.

The oligonucleotides shown below are synthesized:

```
                                            (SEQ ID NO:29)
EXP-A 5'-GGCGAGATCTTGCTGCCCATCATATTGTGC-3'

(SEQ ID NO:30)
EXP-B 5'-GGCGTCTAGACTGCACACCAATGTCAATGT-3'
```

Oligonucleotide EXP-A contains a BglII restriction enzyme recognition site near the 5' end followed by the DNA sequence from nt 425 to nt 445 of SEQ ID NO:1. Oligonucleotide EXP-B contains an XbaI recognition site near the 5' end followed by the reverse complement of the DNA sequence from nt 1471 to nt 1490 of SEQ ID NO:1.

Polymerase chain reaction (PCR) was performed using the oligonucleotides EXP-A and EXP-B as primers and total genomic DNA isolated from Trichoderma reesei strain QM6a (ATCC 13631) as template. The DNA polymerase enzyme (Pwo polymerase), buffer and deoxynucleotide mixture used were supplied by Boehringer Mannheim. The following conditions were used for PCR; step 1, 1 min. at 94° C.; step 2, 40 sec. at 92° C.; step 3, 1 min. at 50° C., step 4, 2 min. at 72° C.; steps 2, 3 and 4 repeated 29 times; step 5, 5 min. at 72° C.

The major DNA product of PCR was a fragment of approximately 1.3 kb as estimated by agarose gel electrophoresis. The PCR product was digested with BglII and XbaI and the 1.3 kb DNA fragment was purified from an agarose electrophoresis gel. This DNA fragment was ligated with pSL1180 (Pharmacia) which had been digested with BglII and XbaI. The resulting plasmid was named pSLexpPCR. DNA sequence analysis confirmed that the 1.3 kb insert in pSLexpPCR corresponded to the expected fragment of the Trichoderma swollenin gene. The DNA sequence revealed the presence of three introns within this 1.3 kb fragment at positions corresponding to between nt 575 and nt 576, between nt 791 and nt 792, and between nt 969 and nt 970 of SEQ ID NO:1.

The plasmid, or the 1.3 kb insert it contains, can now be used as a hybridization probe to allow the entire swollenin gene to be cloned from any genomic DNA or cDNA libraries of interest. The swollenin encoding DNA within the pSLexpPCR does not included the regions corresponding to the CBD or the linker (hinge) region. Therefore, by design, it would be expected to hybridize with other swollenin DNA sequences but not to CBD encoding sequences which may be part of other non-swollenin genes.

Total genomic DNA from T. reesei (longibrachiatum) strain QM6a was digested separately with a variety of different restriction endonucleases and subjected to agarose gel electrophoresis. The DNA was subsequently blotted to a Nytran (S&S) membrane filter and probed with the 1.3 kb BglII-XbaI DNA fragment isolated from pSLexpPCR and labeled with $^{32}P$ by the Megaprime random labeling system supplied by Amersham. Hybridization with the probe was performed at moderate stringency in a buffer containing 30% formamide, 5×SSPE, 0.5% SDS at 38° C. The membrane filter was subsequently washed at moderate stringency in 2×SSC, 0.1% SDS at 55° C. before being exposed to X-ray film. The results indicated that the genomic copy of the T. reesei swollenin gene resides on an approximately 4.5 kb BglII fragment, or on an approximately 5.5 kb XbaI fragment.

Given the exemplified swollenin gene as provided above, it would be routine for one of skill in the art to clone the Trichoderma reesei swollenin gene from genomic DNA or cDNA libraries by colony hybridization using the PCR fragment inserted in pSLexpPCR as a probe.

EXAMPLE 3

Cloning the Genomic Copy of T. Reesei Swollenin and Expression of it in Aspergillus niger var. awamori The genomic copy of T. reesei swollenin was cloned by PCR. The template DNA was from T. reesei RutC-30 (ATCC 56765) and the primers corresponding to the 5' and 3' ends of the swollenin coding region were designated as GCI-PVS-055 (gcg cag atc tca gca atg gct ggt aag ctt atc ctc g SEQ ID NO: 31) and GCI-PVS-056 (gcg ctc tag atc aat tct ggc taa act gca cac c SEQ ID NO:32).

The PCR-amplified fragment was digested with BglII and XbaI and cloned into a BglII-XbaI opened pGAPT-PT resulting in pGAPT-expC. Sequencing the insert revealed that the chromosomal copy of the swollenin gene has five introns.

The chromosomal copy of the swollenin gene (i.e. pGAPT-expC) was transformed into Aspergillus and transformants were screened as described above for the cDNA.

EXAMPLE 4

Method of Isolating DNA Sequences Encoding Swollenins in Microorganisms

Figure 4A:
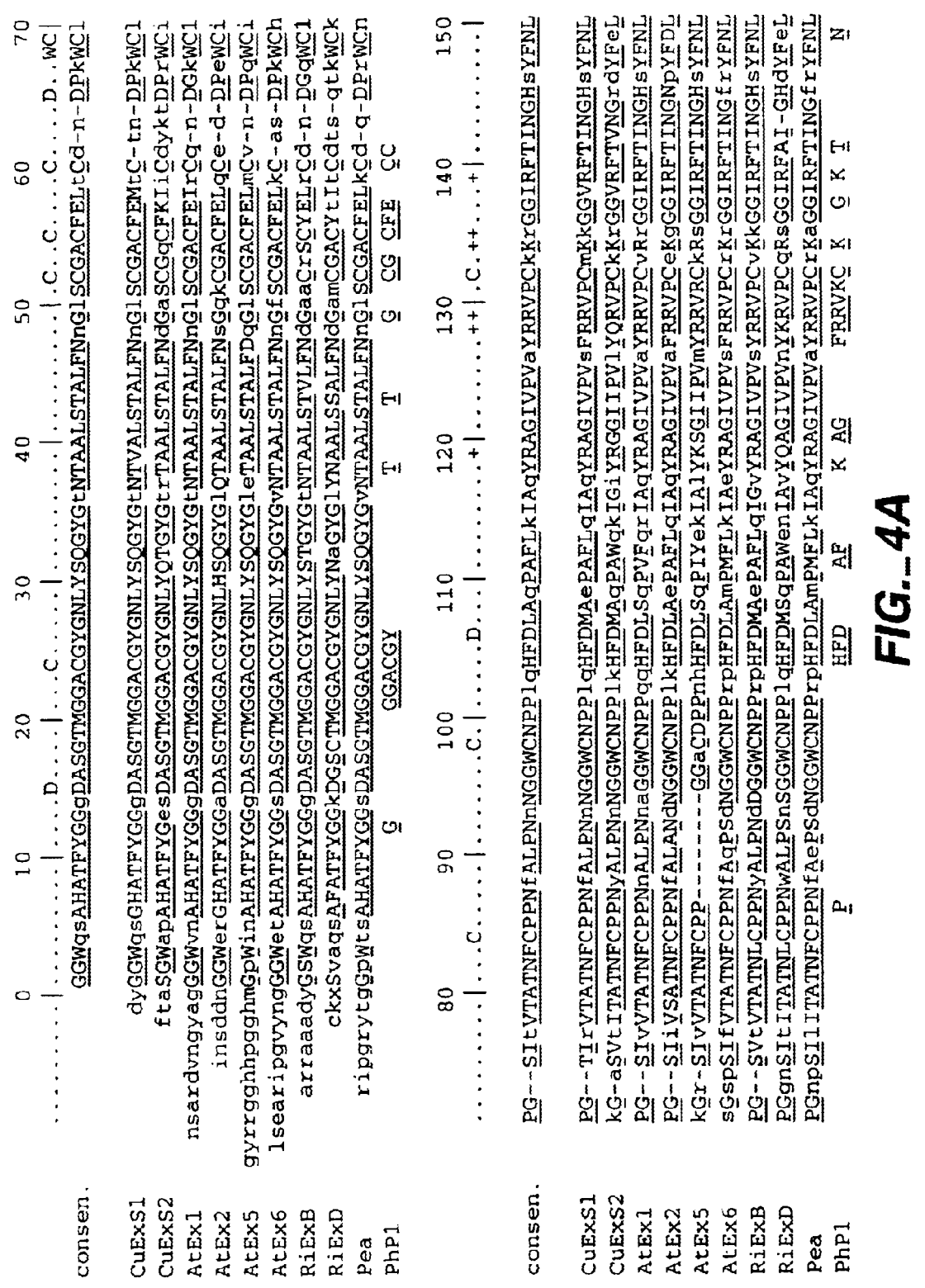

The general technique in Examples 2 and 3 may be adapted in conjunction with known techniques to obtain clones comprising swollenin or swollenin-type genes from other fungi and bacteria. Plasmid pSLexpPCR or the isolated 1.3 kb DNA insert encoding part of the swollenin gene (Example 2), may be labelled as can the core region of the swollenin (Example 3). This DNA probe can then be used to hybridize with genomic DNA or cDNA from other fungi or bacteria. Sequences which have been published for higher plant expansins show a very high level of amino acid identity (see, e.g., FIG. 4, where underlined segments indicate regions of high homology). A comparison of the deduced amino acid sequence of the Trichoderma swollenin with the known amino acid sequences of higher plant expansins identifies certain conserved regions of amino acids between the swollenins and plant expansins. These conserved regions provide the basis for designing degenerate primers for use in PCR amplification of swollenin-encoding DNA from other microorganisms. Such methods are generally known in the art and considered routine (see e.g., McPherson et al., PCR A Practical Approach, pp. 171–186 (1991)). Conserved regions corresponding to amino acids 192–200 and 366–371 of SEQ ID NO:2 are pointed to as being particularly useful for this purpose (see also, highlighted segments of FIG. 2 although other conserved regions could be used.

The sequence at amino acid residues 192–200 of SEQ ID NO:2, TSGGACGFG (SEQ. ID NO:33), is highly homologous to the corresponding sequence in the consensus plant expansin sequence TMGGACGYG (SEQ. ID NO. 34) (numbered positions 19–27 in FIG. 4). Based on this region of homology, it would be possible to synthesize degenerate oligonucleotides comprising all possible DNA sequences which encode part or all of the amino acid sequence T(M/S)GGACG(Y/F)G (SEQ ID NO:35) (see e.g., McPherson et al., supra, page 174).

The sequence at amino acid residues 366 to 371 of SEQ ID:NO.2, YRRVQC (SEQ. ID NO. 36), is highly homologous to the corresponding sequence in the consensus plant expansin sequences YRRVPC (SEQ ID. NO:37) and FRRVPC (SEQ. ID NO: 38) (numbered positions 127–132 in FIG. 4). Based on this region of homology, it would also be possible to synthesize degenerate oligonucleotides to include all possible DNA sequences which encode part or all of the amino acid sequence (F/Y)RRV(P/Q)C (SEQ ID NO:39). The oligonucleotides derived from this amino acid sequence would be used in conjunction with those derived from the previous mentioned amino acid sequence as primers for routine PCR experiments using genomic DNA. Genomic DNA or cDNA could then easily be obtained from any microbe and used as a template in such PCR experiments. In this way it would be possible to clone genes encoding swollenins from a variety of microbes.

EXAMPLE 5

Heterologous Hybridization Method for Isolating Swollenin Encoding Sequences from Other Microorganisms Genomic DNA from different microorganisms was digested with Hind3 and run on 1.0% agarose gel. Gel was depurinated, denatured and blotted, and the membrane was UV-crosslinked as described on page 6. Prehybridization, hybridization, labeling of the probe and detection were done using the DIG/Genius™ System from Boehringer Mannheim.

The probe corresponded to the sequence encoding the core region of T. reesei swollenin. The original cDNA subclone (EXAMPLE 1) was digested with Nco1 and EcoR1 resulting in a 312 bp DNA fragment which was labeled with DIG-dUTP (dioxigenin-dUTP) via random-primed labeling according to manufacturer's (Boehringer Mannheim) instructions.

The membrane was prehybridized and hybridized in 5×SSC–0.1% N-lauroylsarcosine–0.02% SDS–1% Genius™ blocking reagent at 45° C. Hybridization (over night) was followed by two 10 minute washes in 6×SSC at room temperature and two 5 minute washes in 6×SSC at 45° C. Detection with an anti-DIG-alkaline phosphatase conjugate and visualization with a chemiluminescence substrate CSPD® were done according to manufacturer's instructions.

Results from this experiment indicated that at least the following species, in addition to T. reesei, hybridize to the probe: Trichoderma koningii, Hypocrea lenta and Hypocrea schweinitzii. In this Hind3 digestion T. reesei and T. koningii had a over 5 kb band that hybridized with the T. reesei swollenin gene. For H. schweinitzii, the band that hybridized was 3.7 kb and for H. lenta approximately 3.3 kb in size. This method and variations of it (different hybridization and washing conditions) can be used to detect swollenin encoding genes from any organism.

EXAMPLE 6

Preparation Of A Saccharomyces cerevisiae Clone For Expression Of T. reesei Swollenin During the course of obtaining the Trichoderma reesei cDNA mentioned in Example 1, a Saccharomyces cerevisiae clone was obtained which contained an expression plasmid in which the cDNA sequence of SEQ ID NO:1 was inserted between the S. cerevisiae PGK1 promoter and the terminator region in plasmid pAJ401 (Saloheimo et al., 1994, Molec. Microbiol., Vol. 13, pp. 219–228 (1994)) according to the method described by Margolles-Clark et al., (Appl. Environ. Microbiol., 62:3840–3846, 1996). Briefly, T. reesei cDNA was ligated to the EcoRI-XhoI cut plasmid pAJ401. Plasmid pAJ401 was derived from plasmid pFL60 (Minet and Lacroute, Curr. Genet., Vol. 18, pp. 287–291 (1990) by changing the two cloning sites EcoRI and XhoI between the yeast PGK promoter and terminator into the reverse orientation using specific linkers. Transformation of E. coli strain JS4 by electroporation (Bio-Rad) according to the manufacturer's instructions yields a library of $1.3 \times 10^6$ independent clones. One of these clones contained pAJ401 with the cDNA of SEQ ID NO:1 inserted between the EcoRI and XhoI sites and was subsequently transformed into S. cerevisiae strain DBY746. A second yeast clone was obtained which contained pAJ401 without the cDNA sequence of SEQ ID NO:1 for use as a control in Examples 5 and 6.

The two yeast clones, one control clone and one clone containing the T. reesei (longibrachiatum) swollenin cDNA sequence, were cultured for 2–3 days in fermentors. Either Chemap CMF mini 1 liter or Biolafitte 14L fermentors were used. The culture medium was synthetic complete medium without uracil (Sherman, 1991, Methods Enzymol. 194, 3–21). pH was maintained at 5.0, aeration rate was 1 L/min for the smaller fermentors and 8 L/min for the larger fermentors, and agilation speed was 300–600 rpm. Following fermentation, the cells were removed by centrifugation and the supernatant was concentrated 50–100 fold.

EXAMPLE 7

Expression of T. reesei Swollenin cDNA in Aspergillus niger var. awamori

Construction of the Aspergillus Expression Vector

Construction of the Aspergillus expression vector for expression of T. reesei swollenin cDNA consisted of three steps: (1) PCR-amplification of the swollenin cDNA and subcloning it into pSP73-hind3 (i.e. HindIII site was killed), (2) exchanging the middle part of the PCR-derived swollenin gene to the original swollenin gene from the cDNA subclone in order to eliminate mistakes derived from PCR-amplification, and (3) subcloning the swollenin-insert into a Aspergillus expression vector pGAPT-PT for expression under the A. niger var. awamori glaA promoter (glucoamylase).

1. PCR-amplification of the swollenin cDNA:
Primers ExAspBgl2 (CATTAGATCTCAGCAATGGCTGGTAAGCTTATCCTC SEQ ID NO:25) and ExAspXba1 (CGACTCTAGAAGGATTAGTTCTGGCTAAACTGCA CACC SEQ ID NO:26) were used for PCR-amplification of the coding region of the T. reesei swollenin cDNA (vector from example 1).

ExAspBgl2 has a BglII cloning site which is followed by the five last nucleotides of the glaA (glucoamylase) promoter sequence which precede the translation start site (ATG). The ATG in ExAspBgl2 is followed by a 19-mer corresponding to the swollenin signal sequence. ExAspXba1 has a XbaI cloning site, a STOP codon and a sequence which codes for the last 7 codons of the swollenin gene.

The PCR-amplified 1.5 kb swollenin fragment was digested with BglII and XbaI and ligated into BglII-XbaI opened pSP73-Hind3 vector. Before this cloning step pSP73 (Promega) was first deleted for its HindIII site. This was done by opening the vector (pSP73) with HindIII and the protruding ends were filled in with T4 polymerase (with dNTPs), before ligating the vector back together. This vector was designated as pSP73-Hind3.

pSP73-Hind3 containing the 1.5 kb swollenin insert was designated as pPCRAexp.

2. Replacing the PCR-amplified sequence with the original sequence:

pPCRAexp was digested with HindIII and BstEII. HindIII cuts the swollenin coding sequence within the signal sequence and BstEII is close to the end of the swollenin coding sequence. The 1.4 kb HindIII-BstEII swollenin fragment from pPCRAexp was discarded and replaced with the 1.4 kb HindIII-BstEII swollenin fragment from the original swollenin cDNA subclone (EXAMPLE 1). The resultant vector was designated as pWTAexp.

3. Cloning into the expression vector:

pWTAexp was digested with BglII and XbaI resulting in a 1.5 kb swollenin insert with a complete coding region preceded by five nucleotides of the glaA promoter sequence and flanked by cloning sites enabling ligation between the glaA promoter and terminator sequences in a *Aspergillus* expression vector pGAPT-PG (described below). The insert and vector sequences were ligated and the resultant vector was designated as pGAPT-exp (6.5 kb). This is the vector for expressing *T. reesei* swollenin cDNA in *A. niger*.

The expression vector pGAPT-PG (5.1 kb) used for construction of pGAPT-exp consists of a 1.1 kb SpeI-BglII fragment of *A. niger* var. *awamori* glaA promoter sequence, 0.2 kb fragment of *A. niger* glaA terminator sequence and 1.6 kb *A. nidulans* pyrG marker gene in pUC18 backbone. The glaA terminator fragment follows the glaA promoter sequence and is separated from it by multiple cloning sites which can be used for inserting sequences to be expressed.

The 3' end of the glaA promoter sequence, i.e. the sequence preceding the translation start site of the swollenin gene in pGAPT-exp has been engineered (multiple cloning sites) and has the following sequence starting from a XmnI site in the glaA promoter:

GAAGTGCTTCCTCCCTTTTAGACG-
CAACTGAGAGCCTGAGCTTCATCCCCAG-
CATCATTAGATCTCAGCAATG (SEQ ID NO:40)

in which the ATG in the end is the start codon for the swollenin cDNA.

The surrounding sequence of the STOP codon is following (starting from the 'TAA' stop codon—engineered from the original 'TGA' STOP codon in swollenin):
TAATCCTTCTAGAGTCGACCGCGACGGTGACC
shown up till the BstEII site (GGTGACC) in the glaA terminator sequence.

Transformation of pGAPT-exp to *Aspergillus* pGAPT-exp was transferred to the strain *A. niger* var. *awamori* dgr246 p2 described in Ward et al. *Appl. Microbiol. Biotechnol.* 39:738–743 (1993). Transformation of *Aspergillus* follows the same basic procedure as described for *Trichoderma* on pages 13–15. The transformation procedure of *A. niger* var. *awamori* dgr246 p2 is also described in Ward et al. *Appl. Microbiol. Biotechnol.* 39:738–743 (1993).

Transformants were selected on their ability to grow on minimal nutrients without uridine. The untransformed cells require uridine for growth.

Screening of Transformants

*Aspergillus* transformants were cultivated in 50 ml liquid medium in 250 ml shake flasks for 5–11 days as described in Ward et al. *Bio/Technology* 8:435–440 (1990). The complex medium contained 15% maltose to induce the glaA promoter and therefore drive expression of the swollenin gene. Culture supernatants were run on SDS-PAGE gels. *Aspergillus* transformants which were producing the *T. reesei* swollenin had a band running above the 66 kD marker band and this band was missing from lanes of the negative control (*Aspergillus* strain before the transformation) (FIG. 6).

EXAMPLE 8

Effect Of Treatment With *Trichoderma reesei* Swollenin on Cellulose Structure

Whatman No. 3 filter paper circles were cut into strips measuring 2×7 cm. Buffer used was 50 mM sodium acetate, pH 5. The filter paper strips were soaked for at least 30 min. at room temperature in solutions consisting of water, buffer, 8M urea in buffer, or broth produced from yeast cones containing the *T. reesei* swollenin gene or a control yeast clone which does not produce *T. reesei* swollenin in buffer (dilutions ranged from 1 ml of broth in 7 ml buffer to 4 ml broth in 4 ml buffer).

A Thwing-Albert tensile tester was set for a test speed of 0.10 cm/min and tensile energy measured over a range of 0 to 50 lbs. Each strip of filter paper was placed between the clamps and the peak load was measured. The results of this experiment quantify the degree of load that can be held before breaking the paper. Two or three strips were measured for each sample type. The results from several different experiments are given below in Tables 1 and 2.

TABLE 1

| Sample | Trial 1 | Trial 2 | Trial 3 | Average |
|---|---|---|---|---|
| buffer | .55 | .58 | .59 | .57 |
| 8M urea | N/A | .36 | .32 | .34 |
| control broth | .49 | .49 | .47 | .48 |
| swo broth | .40 | .42 | .42 | .41 |

TABLE 2

| Sample | Trial 4 | Trial 5 | Average |
|---|---|---|---|
| buffer | .56 | .59 | .58 |
| 8M urea | .42 | .41 | .42 |
| control 1 ml | .52 | .52 | .52 |
| control 3 ml | .52 | .47 | .50 |
| swo 1 ml | .43 | .42 | .43 |
| swo 3 ml | .46 | .40 | .43 |

As expected, the strips treated with 8M urea, which is known to disrupt hydrogen bonding interactions, cannot hold as high of a load without breaking as strips treated with buffer only. In both experiments, the strips treated with the swollenin broth have a significantly lower maximal load (about 15%) than the strips treated with control broth. The only difference between these two broths is that one is from the fermentation of the yeast strain containing the *T. reesei* swollenin gene, while the control strain does not contain this gene. These results show that there is a component in the swollenin broth which is weakening filter paper.

EXAMPLE 9

Treatment of Cotton Fibers with Swollenin

The yeast clones described above in Example 4 were grown under the conditions specified and the fermentation broth separated from extraneous cell matter and debris. A control clone of yeast, which contained the expression plasmid but without the inserted swollenin encoding cDNA sequence, was also grown under the same conditions and the fermentation broth isolated by removing extraneous cell matter and debris. The culture supernatants from two fermentations, one containing yeast transformed with the swollenin gene and one containing yeast transformed without the swollenin gene as a control, were concentrated approximately 50 fold and were used to determine the effects of incubating *T. reesei* swollenin with cotton fibers. The effects of the two supernatants were further compared with the cellobiohydrolase I (CBHI) for *T. reesei*.

Mercerized cotton fibers were suspended in buffer (50 mM sodium acetate, pH 5.0) containing supernatant from the yeast fermentations (dilution 1:4) and CBHI (dosage 5 μg/g). After incubation for 240 minutes at 25° C., the suspended fibers were filtered off and the amount of reducing sugars released into the filtrates was determined by the method of Sumner and Somers (1944). The fibers were rinsed once with buffer and then suspended in distilled water with glass beads prior to sonication for one minute using a probe tip sonicator (Vibra Cell Sonics and Materials Inc.) The fibers were then stained and visualized by light microscopy to determine gross affects on their structure. The filtrate from the control treatment and the filtrate originating from the yeast strain containing the swollenin gene did not exhibit hydrolytic activity, that is, no reducing sugars were liberated from the cotton fibers. In contrast, CBHI alone liberated reducing sugars 0.08% (of original dry weight). Prior to sonication no difference between fibers treated with supernatant from the control yeast strain versus fibers treated with supernatant from the yeast strain containing the swollenin gene could be discerned. However, after sonication swollen and disorganized regions were apparent in fibers treated with supernatant from the yeast containing the swollenin gene which were not present in the fibers treated with supernatant obtained from the control yeast strain (FIG. 5). CBHI alone caused light fibrillation on the fibers, but no opened and swollen regions, which were typical effects for supernatant from yeast containing the swollenin gene, were detected.

We claim:

1. An isolated DNA encoding a microbial swollenin protein, wherein said swollenin protein comprises the amino acid sequence set forth in SEQ ID NO: 2.

2. The DNA according to claim 1, wherein said DNA is obtained from *Trichoderma reesei*.

3. A DNA according to claim 1, wherein said DNA hybridizes under moderate stringency conditions with a DNA comprising the nucleic acid sequence set forth in SEQ ID NO: 1.

4. A DNA according claim 3, wherein said DNA hybridizes under moderate stringency conditions with a DNA probe encoding a peptide having an amino acid sequence comprising SEQ ID NO:33, SEQ ID NO:34, SEQ ID NO:36, SEQ ID NO:37, or SEQ ID NO:38.

5. A DNA according to claim 1 comprising the nucleic acid sequence set forth in SEQ ID NO: 1.

6. A vector comprising the DNA of claim 1.

7. A host cell transformed with the vector of claim 6.

8. The host cell according to claim 7, wherein said host cell has been genetically altered to delete one or more cellulase genes.

9. The host cell according to claim 7, wherein said host cell is a filamentous fungus.

10. The host cell according to claim 9, wherein said filamentous fungus is *Trichoderma* spp., *Humicola* spp., *Neurospora* spp., *Aspergillus* spp., or *Fusarium* spp.

11. A method of producing swollenin protein comprising the steps of:

(a) obtaining a host cell which has been transformed with a vector comprising DNA encoding a swollenin protein, wherein said DNA is isolated from *T. reesei*;

(b) culturing said host cell in fermentation broth, under conditions suitable for the expression and, optionally, secretion, of said swollenin protein;

(c) recovering said swollenin protein from said fermentation broth.

12. The method according to claim 11, wherein said DNA hybridizes under moderate stringency conditions with a DNA comprising the nucleic acid sequence set forth in SEQ ID NO: 1.

13. The method according to claim 11, wherein said DNA hybridizes under moderate stringency conditions with a DNA probe encoding a peptide having an amino acid sequence comprising SEQ ID NO:33, SEQ ID NO:34, SEQ ID NO:36, SEQ ID NO:37, or SEQ ID NO:38.

14. The method according to claim 11, wherein said DNA comprises the nucleic acid sequence set forth in SEQ ID NO: 1.

* * * * *

SEQUENCE LISTING

<160> NUMBER OF SEQ ID NOS: 40

<210> SEQ ID NO 1
<211> LENGTH: 1952
<212> TYPE: DNA
<213> ORGANISM: Trichoderma reesei

<400> SEQUENCE: 1

```
ggcacgagga actgttagac gggatggctg gtaagcttat cctcgtggct ctagcaagcc      60
ttgtatcact ctctattcag cagaattgcg cagcattatt gtaagagtgt tgagcgtgtt     120
gagtaccatc tgtatcgttg ctaacgtagg cttttagtgg ccaatgtgga ggcatagggt     180
ggtccggcac cacatgttgc gttgctggcg cccagtgcag ttttgtcaat gactggtact     240
cccagtgcct tgcgtcaacc gtatgagctc cgatccgggc cgtcaatatc ttctaactcc     300
agactgtaca gggcggaaac cccccaaacg gaacaacttc ctctagcttg gtttcacgga     360
cgtcgtcagc atcctcatcc gtcggctcgt cttcacccgg cggcaactca ccaactggca     420
gtgcttccac ctacacaacc acagatacag ctaccgtggc tcctcattcg cagtctcctt     480
accccagcat tgccgcatcc agttgcggat cgtggaccct cgtggataat gtttgctgcc     540
catcatattg tgctaatgat gacacatccg agtcatgctc aggctgcggt acctgcacta     600
cgccgccctc ggcggactgc aaatccggaa ccatgtatcc agaggtccat cacgtatcca     660
gcaacgagag ctggcactac agtgtaagat gaccaacgct ggggtatcta atcctttgtc     720
ttcctcggcg tgctgaccct ggagcattta gagatcaacc cactttggcc taacgagcgg     780
cggggcctgt ggctttggcc tgtacggtct ctgcacaaag ggcagtgtta cagccagctg     840
gacggatccc atgcttggcg cgacgtgtga cgcttttttgt acagcgtatc ccctgctttg     900
caaagaccct accggcacta cccttcgtgg caacttcgca gctccaaacg gcgattacta     960
```

-continued

```
cacccaagtt ggggaccccg agaggcaatc attttctggt gtagtattca ctgacagtgc    1020
gatagttctg gtcctcgttg ccaggagccc tcgataacta cctgtcctgc ggcgagtgca    1080
ttgagctgat acaaacaaag cccgatggga ccgattatgc tgtcggagaa gccggctaca    1140
cggatccaat tactctcgag attgtggaca gctgcccgtg cagcgcgaac tccaagtggt    1200
gctgtcagag agccccgtcc atcccgtcca ttgtactaca tgcgccaacc gaatggccct    1260
ggctaacatc tcgcaggtgg tccgggcgcc gatcattgcg agagatcga cttcaaatac     1320
ggctgtcctc ttcctgctga cagcattcat ctcgacctgt cagacattgc catgggccgt    1380
ttgcagggca atggatcact aaccaatggc gtcatcccga ctcgatatag aagagtccaa    1440
tgccccaaag ttgggaacgc ctacatttgg cttcgaaatg cggagggcc ttactatttt     1500
gctctcacgg cagtcaacac caacggaccg ggctcagtca ccaaaatcga gatcaagggc    1560
gcagacaccg acaactgggt tgccttggtc catgacccaa actatacgag tagccgccca    1620
caagaacgct atggcagttg gtaatcccca cagggatcag ggccctttaa cttgcctgtt    1680
ggaattcgtc tgactagccc aacgggggaa cagattgtga atgaacaggc catcaagaca    1740
ttcactcctc cggccacagg tgaccccaat ttttactaca ttgacattgg tgtgcagttt    1800
agccagaatt gatggcaagc attgggcaat gggcttcttg ctgtgggaca atgatgtagg    1860
ctagattctc aatgcttcaa gtatgtggtg tacgtcttcg tgtgtataga taggtatgct    1920
gttcacttaa atacacatcc tttggtacgt tg                                  1952
```

<210> SEQ ID NO 2
<211> LENGTH: 493
<212> TYPE: PRT
<213> ORGANISM: Trichoderma reesei

<400> SEQUENCE: 2

```
Met Ala Gly Lys Leu Ile Leu Val Ala Leu Ala Ser Leu Val Ser Leu
 1               5                  10                  15

Ser Ile Gln Gln Asn Cys Ala Ala Leu Phe Gly Gln Cys Gly Gly Ile
            20                  25                  30

Gly Trp Ser Gly Thr Thr Cys Cys Val Ala Gly Ala Gln Cys Ser Phe
        35                  40                  45

Val Asn Asp Trp Tyr Ser Gln Cys Leu Ala Ser Thr Gly Gly Asn Pro
    50                  55                  60

Pro Asn Gly Thr Thr Ser Ser Ser Leu Val Ser Arg Thr Ser Ser Ala
65                  70                  75                  80

Ser Ser Ser Val Gly Ser Ser Pro Gly Gly Asn Ser Pro Thr Gly
                85                  90                  95

Ser Ala Ser Thr Tyr Thr Thr Thr Asp Thr Ala Thr Val Ala Pro His
            100                 105                 110

Ser Gln Ser Pro Tyr Pro Ser Ile Ala Ala Ser Ser Cys Gly Ser Trp
        115                 120                 125

Thr Leu Val Asp Asn Val Cys Cys Pro Ser Tyr Cys Ala Asn Asp Asp
    130                 135                 140

Thr Ser Glu Ser Cys Ser Gly Cys Gly Thr Cys Thr Thr Pro Pro Ser
145                 150                 155                 160

Ala Asp Cys Lys Ser Gly Thr Met Tyr Pro Glu Val His His Val Ser
                165                 170                 175

Ser Asn Glu Ser Trp His Tyr Ser Arg Ser Thr His Phe Gly Leu Thr
            180                 185                 190

Ser Gly Gly Ala Cys Gly Phe Gly Leu Tyr Gly Leu Cys Thr Lys Gly
```

```
                    195                 200                 205
Ser Val Thr Ala Ser Trp Thr Asp Pro Met Leu Gly Ala Thr Cys Asp
    210                 215                 220

Ala Phe Cys Thr Ala Tyr Pro Leu Leu Cys Lys Asp Pro Thr Gly Thr
225                 230                 235                 240

Thr Leu Arg Gly Asn Phe Ala Ala Pro Asn Gly Asp Tyr Tyr Thr Gln
                245                 250                 255

Phe Trp Ser Ser Leu Pro Gly Ala Leu Asp Asn Tyr Leu Ser Cys Gly
            260                 265                 270

Glu Cys Ile Glu Leu Ile Gln Thr Lys Pro Asp Gly Thr Asp Tyr Ala
        275                 280                 285

Val Gly Glu Ala Gly Tyr Thr Asp Pro Ile Thr Leu Glu Ile Val Asp
    290                 295                 300

Ser Cys Pro Cys Ser Ala Asn Ser Lys Trp Cys Cys Gly Pro Gly Ala
305                 310                 315                 320

Asp His Cys Gly Glu Ile Asp Phe Lys Tyr Gly Cys Pro Leu Pro Ala
                325                 330                 335

Asp Ser Ile His Leu Asp Leu Ser Asp Ile Ala Met Gly Arg Leu Gln
            340                 345                 350

Gly Asn Gly Ser Leu Thr Asn Gly Val Ile Pro Thr Arg Tyr Arg Arg
        355                 360                 365

Val Gln Cys Pro Lys Val Gly Asn Ala Tyr Ile Trp Leu Arg Asn Gly
    370                 375                 380

Gly Gly Pro Tyr Tyr Phe Ala Leu Thr Ala Val Asn Thr Asn Gly Pro
385                 390                 395                 400

Gly Ser Val Thr Lys Ile Glu Ile Lys Gly Ala Asp Thr Asp Asn Trp
                405                 410                 415

Val Ala Leu Val His Asp Pro Asn Tyr Thr Ser Ser Arg Pro Gln Glu
            420                 425                 430

Arg Tyr Gly Ser Trp Val Ile Pro Gln Gly Ser Gly Pro Phe Asn Leu
        435                 440                 445

Pro Val Gly Ile Arg Leu Thr Ser Pro Thr Gly Glu Gln Ile Val Asn
    450                 455                 460

Glu Gln Ala Ile Lys Thr Phe Thr Pro Ala Thr Gly Asp Pro Asn
465                 470                 475                 480

Phe Tyr Tyr Ile Asp Ile Gly Val Gln Phe Ser Gln Asn
                485                 490

<210> SEQ ID NO 3
<211> LENGTH: 322
<212> TYPE: PRT
<213> ORGANISM: Plant/eukaryotic

<400> SEQUENCE: 3

Val His His Val Ser Ser Asn Glu Ser Trp His Tyr Ser Arg Ser Thr
  1               5                  10                  15

His Phe Gly Leu Thr Ser Gly Ala Cys Gly Phe Gly Leu Tyr Gly
            20                  25                  30

Leu Cys Thr Lys Gly Ser Val Thr Ala Ser Trp Thr Asp Pro Met Leu
        35                  40                  45

Gly Ala Thr Cys Asp Ala Phe Cys Thr Ala Tyr Pro Leu Leu Cys Lys
    50                  55                  60

Asp Pro Thr Gly Thr Thr Leu Arg Gly Asn Phe Ala Ala Pro Asn Gly
65                  70                  75                  80
```

```
Asp Tyr Tyr Thr Gln Phe Trp Ser Ser Leu Pro Gly Ala Leu Asp Asn
             85                  90                  95

Tyr Leu Ser Cys Gly Glu Cys Ile Glu Leu Ile Gln Thr Lys Pro Asp
            100                 105                 110

Gly Thr Asp Tyr Ala Val Gly Glu Ala Gly Tyr Thr Asp Pro Ile Thr
        115                 120                 125

Leu Glu Ile Val Asp Ser Cys Pro Cys Ser Ala Asn Ser Lys Trp Cys
130                 135                 140

Cys Gly Pro Gly Ala Asp His Cys Gly Glu Ile Asp Phe Lys Tyr Gly
145                 150                 155                 160

Cys Pro Leu Pro Ala Asp Ser Ile His Leu Asp Leu Ser Asp Ile Ala
                165                 170                 175

Met Gly Arg Leu Gln Gly Asn Gly Ser Leu Thr Asn Gly Val Ile Pro
            180                 185                 190

Thr Arg Tyr Arg Arg Val Gln Cys Pro Lys Val Gly Asn Ala Tyr Ile
        195                 200                 205

Trp Leu Arg Asn Gly Gly Pro Tyr Tyr Phe Ala Leu Thr Ala Val
210                 215                 220

Asn Thr Asn Gly Pro Gly Ser Val Thr Lys Ile Glu Ile Lys Gly Ala
225                 230                 235                 240

Asp Thr Asp Asn Trp Val Ala Leu Val His Asp Pro Asn Tyr Thr Ser
                245                 250                 255

Ser Arg Pro Gln Glu Arg Tyr Gly Ser Trp Val Ile Pro Gln Gly Ser
            260                 265                 270

Gly Pro Phe Asn Leu Pro Val Gly Ile Arg Leu Thr Ser Pro Thr Gly
        275                 280                 285

Glu Gln Ile Val Asn Glu Gln Ala Ile Lys Thr Phe Thr Pro Pro Ala
    290                 295                 300

Thr Gly Asp Pro Asn Phe Tyr Tyr Ile Asp Ile Gly Val Gln Phe Ser
305                 310                 315                 320

Gln Asn

<210> SEQ ID NO 4
<211> LENGTH: 223
<212> TYPE: PRT
<213> ORGANISM: Trichoderma reesei

<400> SEQUENCE: 4

Gly Gly Trp Gln Ser Ala His Ala Thr Phe Tyr Gly Gly Gly Asp Ala
  1               5                  10                  15

Ser Gly Thr Met Gly Gly Ala Cys Gly Tyr Gly Asn Leu Tyr Ser Gln
             20                  25                  30

Gly Tyr Gly Thr Asn Thr Ala Ala Leu Ser Thr Ala Leu Phe Asn Asn
         35                  40                  45

Gly Leu Ser Cys Gly Ala Cys Phe Glu Leu Thr Cys Asp Asn Asp Pro
     50                  55                  60

Lys Trp Cys Leu Pro Gly Ser Ile Thr Val Thr Ala Thr Asn Phe Cys
65                  70                  75                  80

Pro Pro Asn Phe Ala Leu Pro Asn Asn Gly Gly Trp Cys Asn Pro
                85                  90                  95

Pro Leu Gln His Phe Asp Leu Ala Gln Pro Ala Phe Leu Lys Ile Ala
            100                 105                 110

Gln Tyr Arg Ala Gly Ile Val Pro Val Ala Tyr Arg Arg Val Pro Cys
        115                 120                 125
```

```
Lys Lys Arg Gly Gly Ile Arg Phe Thr Ile Asn Gly His Ser Tyr Phe
130                 135                 140

Asn Leu Val Leu Ile Thr Asn Val Gly Gly Ala Gly Asp Val His Ser
145                 150                 155                 160

Val Ser Ile Lys Gly Ser Arg Thr Gly Trp Gln Ala Met Ser Arg Asn
            165                 170                 175

Trp Gly Gln Asn Trp Gln Ser Asn Ser Tyr Leu Asn Gly Gln Ser Leu
                180                 185                 190

Ser Phe Gln Val Thr Leu Ser Asp Gly Arg Thr Val Thr Ser Asn Val
        195                 200                 205

Ala Pro Ala Asn Trp Gln Phe Gly Gln Thr Phe Gly Gly Gln Phe
    210                 215                 220
```

<210> SEQ ID NO 5
<211> LENGTH: 222
<212> TYPE: PRT
<213> ORGANISM: Plant/eukaryotic

<400> SEQUENCE: 5

```
Gly Gly Trp Gln Ser Ala His Ala Thr Phe Tyr Gly Gly Asp Ala
1               5                   10                  15

Ser Gly Thr Met Gly Gly Ala Cys Gly Tyr Gly Asn Leu Tyr Ser Gln
                20                  25                  30

Gly Tyr Gly Thr Asn Thr Ala Ala Leu Ser Thr Ala Leu Phe Asn Asn
            35                  40                  45

Gly Leu Ser Cys Gly Ala Cys Phe Glu Leu Thr Cys Asp Asn Asp Pro
    50                  55                  60

Lys Cys Leu Pro Gly Ser Ile Thr Val Thr Ala Thr Asn Phe Cys Pro
65                  70                  75                  80

Pro Asn Phe Ala Leu Pro Asn Asn Gly Gly Trp Cys Asn Pro Pro
                85                  90                  95

Leu Gln His Phe Asp Leu Ala Gln Pro Ala Phe Leu Lys Ile Ala Gln
                100                 105                 110

Tyr Arg Ala Gly Ile Val Pro Val Ala Tyr Arg Arg Val Pro Cys Lys
            115                 120                 125

Lys Arg Gly Gly Ile Arg Phe Thr Ile Asn Gly His Ser Tyr Phe Asn
130                 135                 140

Leu Val Leu Ile Thr Asn Val Gly Gly Ala Gly Asp Val His Ser Val
145                 150                 155                 160

Ser Ile Lys Gly Ser Arg Thr Gly Trp Gln Ala Met Ser Arg Asn Trp
                165                 170                 175

Gly Gln Asn Trp Gln Ser Asn Ser Tyr Leu Asn Gly Gln Ser Leu Ser
            180                 185                 190

Phe Gln Val Thr Leu Ser Asp Gly Arg Thr Val Thr Ser Asn Val Ala
        195                 200                 205

Pro Ala Asn Trp Gln Phe Gly Gln Thr Phe Gly Gly Gln Phe
    210                 215                 220
```

<210> SEQ ID NO 6
<211> LENGTH: 225
<212> TYPE: PRT
<213> ORGANISM: Plant/eukaryotic

<400> SEQUENCE: 6

```
Asp Tyr Gly Gly Asn Gln Ser Gly His Ala Thr Phe Tyr Gly Gly Gly
1               5                   10                  15
```

```
Asp Ala Ser Gly Thr Met Gly Gly Ala Cys Gly Tyr Gly Asn Leu Tyr
            20                  25                  30

Ser Gln Gly Tyr Gly Thr Asn Thr Val Ala Leu Ser Thr Ala Leu Phe
            35                  40                  45

Asn Asn Gly Leu Ser Cys Gly Ala Cys Phe Glu Met Thr Cys Thr Asn
        50                  55                  60

Asp Pro Lys Trp Cys Pro Gly Thr Ile Arg Val Thr Ala Thr Asn Phe
65                  70                  75                  80

Cys Pro Pro Asn Phe Ala Leu Pro Asn Asn Asn Gly Gly Trp Cys Asn
                85                  90                  95

Pro Pro Gln His Phe Asp Met Ala Glu Pro Ala Phe Leu Gln Ile Ala
            100                 105                 110

Gln Tyr Arg Ala Gly Ile Val Pro Val Ser Phe Arg Arg Val Pro Cys
            115                 120                 125

Met Lys Lys Gly Gly Val Arg Phe Thr Ile Asn Gly His Ser Tyr Phe
        130                 135                 140

Asn Leu Val Leu Ile Thr Asn Val Gly Gly Ala Gly Asp Val His Ser
145                 150                 155                 160

Val Ser Ile Lys Gly Ser Arg Thr Gly Trp Gln Ala Met Ser Arg Asn
                165                 170                 175

Trp Gly Gln Asn Trp Gln Ser Asn Asn Tyr Leu Asn Gly Gln Gly Leu
            180                 185                 190

Ser Phe Gln Val Thr Leu Ser Asp Gly Arg Thr Leu Thr Ala Tyr Asn
            195                 200                 205

Leu Val Pro Ser Asn Trp Gln Phe Gly Gln Thr Tyr Glu Gly Pro Gln
            210                 215                 220

Phe
225

<210> SEQ ID NO 7
<211> LENGTH: 234
<212> TYPE: PRT
<213> ORGANISM: Plant/eukaryotic

<400> SEQUENCE: 7

Phe Thr Ala Ser Gly Trp Ala Pro Ala His Ala Thr Phe Tyr Gly Glu
1               5                   10                  15

Ser Asp Ala Ser Gly Thr Met Gly Gly Ala Cys Gly Tyr Gly Asn Leu
            20                  25                  30

Tyr Gln Thr Gly Tyr Gly Thr Arg Thr Ala Ala Leu Ser Thr Ala Leu
            35                  40                  45

Phe Asn Asp Gly Ala Ser Cys Gly Gln Cys Phe Lys Ile Ile Cys Asp
        50                  55                  60

Tyr Lys Thr Asp Pro Arg Trp Cys Ile Lys Gly Ala Ser Val Thr Ile
65                  70                  75                  80

Thr Ala Thr Asn Phe Cys Pro Pro Asn Tyr Ala Leu Pro Asn Asn Asn
                85                  90                  95

Gly Gly Trp Cys Asn Pro Pro Leu Lys His Phe Asp Met Ala Gln Pro
            100                 105                 110

Ala Trp Gln Lys Ile Gly Ile Tyr Arg Gly Gly Ile Ile Pro Val Leu
            115                 120                 125

Tyr Gln Arg Val Pro Cys Lys Lys Arg Gly Gly Val Arg Phe Thr Val
            130                 135                 140

Asn Gly Arg Asp Tyr Phe Glu Leu Val Leu Ile Thr Asn Val Gly Gly
145                 150                 155                 160
```

```
Ala Gly Asp Ile Lys Ser Val Ser Ile Lys Gly Ser Lys Ser Ser Asn
                165                 170                 175

Trp Thr Pro Met Ser Arg Asn Trp Gly Ala Asn Trp Gln Ser Asn Ser
            180                 185                 190

Tyr Leu Asn Gly Gln Ser Leu Ser Phe Lys Val Thr Thr Ser Asp Gly
        195                 200                 205

Gln Val Gln Val Phe Asn Asn Val Val Pro Ser Ser Trp Arg Phe Gly
    210                 215                 220

Gln Thr Phe Ala Ser Lys Val Gln Phe Ser
225                 230

<210> SEQ ID NO 8
<211> LENGTH: 236
<212> TYPE: PRT
<213> ORGANISM: Plant/eukaryotic

<400> SEQUENCE: 8

Asn Ser Ala Arg Asp Val Asn Gly Tyr Ala Gly Gly Trp Val Asn
 1               5                  10                  15

Ala His Ala Thr Phe Tyr Gly Gly Asp Ala Ser Gly Thr Met Gly
             20                 25                  30

Gly Ala Cys Gly Tyr Gly Asn Leu Tyr Ser Gln Gly Tyr Gly Thr Asn
        35                  40                  45

Thr Ala Ala Leu Ser Thr Ala Leu Phe Asn Asn Gly Leu Ser Cys Gly
    50                  55                  60

Ala Cys Phe Glu Ile Arg Cys Gln Asn Asp Gly Lys Trp Cys Pro Gly
65                  70                  75                  80

Ser Ile Val Val Thr Ala Thr Asn Phe Cys Pro Pro Asn Asn Ala Leu
                85                  90                  95

Pro Asn Asn Ala Gly Gly Trp Cys Asn Pro Pro Gln Gln His Phe Asp
            100                 105                 110

Leu Ser Gln Pro Val Phe Gln Arg Ile Ala Gln Tyr Arg Ala Gly Ile
        115                 120                 125

Val Pro Val Ala Tyr Arg Arg Val Pro Cys Val Arg Arg Gly Gly Ile
    130                 135                 140

Arg Phe Thr Ile Asn Gly His Ser Tyr Phe Asn Leu Val Leu Ile Thr
145                 150                 155                 160

Asn Val Gly Gly Ala Gly Asp Val His Ser Ala Met Val Lys Gly Ser
                165                 170                 175

Arg Thr Gly Trp Gln Ala Met Ser Arg Asn Trp Gly Gln Asn Trp Gln
            180                 185                 190

Ser Asn Ser Tyr Leu Asn Gly Gln Ser Leu Ser Phe Lys Val Thr Thr
        195                 200                 205

Ser Asp Gly Gln Thr Ile Val Ser Asn Asn Val Ala Asn Ala Gly Trp
    210                 215                 220

Ser Phe Gly Gln Thr Phe Thr Gly Ala Gln Leu Arg
225                 230                 235

<210> SEQ ID NO 9
<211> LENGTH: 232
<212> TYPE: PRT
<213> ORGANISM: Plant/eukaryotic

<400> SEQUENCE: 9

Ile Asn Ser Asp Asp Asn Gly Gly Trp Glu Arg Gly His Ala Thr Phe
 1               5                  10                  15
```

```
Tyr Gly Gly Ala Asp Ala Ser Gly Thr Met Gly Gly Ala Cys Gly Tyr
            20                  25                  30

Gly Asn Leu His Ser Gln Gly Tyr Gly Leu Gln Thr Ala Ala Leu Ser
            35                  40                  45

Thr Ala Leu Phe Asn Ser Gly Gln Lys Cys Gly Ala Cys Phe Glu Leu
            50                  55                  60

Gln Cys Glu Asp Asp Pro Glu Trp Cys Ile Pro Gly Ser Ile Ile Val
 65                  70                  75                  80

Ser Ala Thr Asn Pro Cys Pro Pro Asn Phe Ala Leu Ala Asn Asp Asn
                85                  90                  95

Gly Gly Trp Cys Asn Pro Pro Leu Lys His Phe Asp Leu Ala Glu Pro
                100                 105                 110

Ala Phe Leu Gln Ile Ala Gln Tyr Arg Ala Gly Ile Val Pro Val Ala
            115                 120                 125

Phe Arg Arg Val Pro Cys Glu Lys Gly Gly Ile Arg Phe Thr Ile
            130                 135                 140

Asn Gly His Pro Tyr Phe Asp Leu Val Leu Ile Thr Asn Val Gly Gly
145                 150                 155                 160

Ala Gly Asp Ile Arg Ala Val Ser Leu Lys Gly Ser Lys Thr Asp Gln
                165                 170                 175

Trp Gln Ser Met Ser Arg Asn Trp Gly Gln Asn Trp Gln Ser Asn Thr
            180                 185                 190

Tyr Leu Arg Gly Gln Ser Leu Ser Phe Gln Val Thr Asp Ser Asp Gly
            195                 200                 205

Arg Thr Val Val Ser Tyr Asp Val Val Pro His Asp Trp Gln Phe Gly
            210                 215                 220

Gln Thr Phe Glu Gly Gly Gln Phe
225                 230

<210> SEQ ID NO 10
<211> LENGTH: 233
<212> TYPE: PRT
<213> ORGANISM: Plant/eukaryotic

<400> SEQUENCE: 10

Gly Tyr Arg Arg Gly Gly His His Pro Gly Gly His Met Gly Pro Trp
 1               5                  10                  15

Ile Asn Ala His Ala Thr Phe Tyr Gly Gly Gly Asp Ala Ser Gly Thr
            20                  25                  30

Met Gly Gly Ala Cys Gly Tyr Gly Asn Leu Tyr Ser Gln Gly Tyr Gly
            35                  40                  45

Leu Glu Thr Ala Ala Leu Ser Thr Ala Leu Phe Asp Gln Gly Leu Ser
            50                  55                  60

Cys Gly Ala Cys Phe Glu Leu Met Cys Val Asn Asp Pro Gln Trp Cys
 65                  70                  75                  80

Ile Lys Gly Arg Ser Ile Val Val Thr Ala Thr Asn Phe Cys Pro Pro
                85                  90                  95

Gly Gly Ala Cys Asp Pro Pro Asn His His Phe Asp Leu Ser Gln Pro
                100                 105                 110

Ile Tyr Glu Lys Ile Ala Leu Tyr Lys Ser Gly Ile Ile Pro Val Met
            115                 120                 125

Tyr Arg Arg Val Arg Cys Lys Arg Ser Gly Gly Ile Arg Phe Thr Ile
            130                 135                 140

Asn Gly His Ser Tyr Phe Asn Leu Val Leu Val Thr Asn Val Gly Gly
```

```
                145                 150                 155                 160
Ala Gly Asp Val His Ser Val Ser Met Lys Gly Ser Arg Thr Lys Trp
                    165                 170                 175
Gln Leu Met Ser Arg Asn Trp Gly Gln Asn Trp Gln Ser Asn Ser Tyr
                    180                 185                 190
Leu Asn Gly Gln Ser Leu Ser Phe Val Val Thr Thr Ser Asp Arg Arg
                    195                 200                 205
Ser Val Val Ser Phe Asn Val Ala Pro Pro Thr Trp Ser Phe Gly Gln
                    210                 215                 220
Thr Tyr Thr Gly Gly Gln Phe Arg Tyr
225                 230

<210> SEQ ID NO 11
<211> LENGTH: 241
<212> TYPE: PRT
<213> ORGANISM: Plant/eukaryotic

<400> SEQUENCE: 11

Leu Ser Glu Ala Arg Ile Pro Gly Val Tyr Asn Gly Gly Trp Glu
  1               5                  10                  15
Thr Ala His Ala Thr Phe Tyr Gly Gly Ser Asp Ala Ser Gly Thr Met
                    20                  25                  30
Gly Gly Ala Cys Gly Tyr Gly Asn Leu Tyr Ser Gln Gly Tyr Gly Val
                    35                  40                  45
Asn Thr Ala Ala Leu Ser Thr Ala Leu Phe Asn Asn Gly Phe Ser Cys
 50                  55                  60
Gly Ala Cys Phe Glu Leu Lys Cys Ala Ser Asp Pro Lys Trp Cys His
 65                  70                  75                  80
Ser Gly Ser Pro Ser Ile Phe Val Thr Ala Thr Asn Phe Cys Pro Pro
                    85                  90                  95
Asn Phe Ala Gln Pro Ser Asp Asn Gly Gly Trp Cys Asn Pro Pro Arg
                    100                 105                 110
Pro His Phe Asp Leu Ala Met Pro Met Phe Leu Lys Ile Ala Glu Tyr
                    115                 120                 125
Arg Ala Gly Ile Val Pro Val Ser Phe Arg Arg Val Pro Cys Arg Lys
                    130                 135                 140
Arg Gly Gly Ile Arg Phe Thr Ile Asn Gly Phe Arg Tyr Phe Asn Leu
145                 150                 155                 160
Val Leu Val Thr Asn Val Ala Gly Ala Gly Asn Ile Val Arg Leu Gly
                    165                 170                 175
Val Lys Gly Thr His Thr Ser Trp Met Thr Met Ser Arg Asn Trp Gly
                    180                 185                 190
Gln Asn Trp Gln Ser Asn Ser Val Leu Val Gly Gln Ser Leu Ser Phe
                    195                 200                 205
Arg Val Thr Ser Ser Asp Arg Arg Ser Ser Thr Ser Trp Asn Ile Ala
                    210                 215                 220
Pro Ala Asn Trp Lys Phe Gly Gln Thr Phe Met Gly Lys Asn Phe Arg
225                 230                 235                 240
Val

<210> SEQ ID NO 12
<211> LENGTH: 233
<212> TYPE: PRT
<213> ORGANISM: Plant/eukaryotic
<220> FEATURE:
<221> NAME/KEY: VARIANT
```

```
<222> LOCATION: (1)...(233)
<223> OTHER INFORMATION: Xaa = Any Amino Acid

<400> SEQUENCE: 12

Ala Arg Arg Ala Ala Ala Asp Tyr Gly Ser Trp Gln Ser Ala His Ala
 1               5                  10                  15

Thr Phe Tyr Gly Gly Gly Asp Ala Ser Gly Thr Met Gly Gly Ala Cys
             20                  25                  30

Gly Tyr Gly Asn Leu Tyr Ser Thr Gly Tyr Gly Thr Asn Thr Ala Ala
             35                  40                  45

Leu Ser Thr Val Leu Phe Asn Asp Gly Ala Ala Cys Arg Ser Cys Tyr
 50                  55                  60

Glu Leu Arg Cys Asp Asn Asp Gly Gln Trp Cys Leu Pro Gly Ser Val
65                  70                  75                  80

Thr Val Thr Ala Thr Asn Leu Cys Pro Pro Asn Tyr Ala Leu Pro Asn
                 85                  90                  95

Asp Asp Gly Gly Trp Cys Asn Pro Pro Arg Pro His Phe Asp Met Ala
            100                 105                 110

Glu Pro Ala Phe Leu Gln Ile Gly Val Tyr Arg Ala Gly Ile Val Pro
            115                 120                 125

Val Ser Tyr Arg Arg Val Pro Cys Val Lys Lys Gly Gly Ile Arg Phe
130                 135                 140

Thr Ile Asn Gly His Ser Tyr Phe Asn Leu Val Leu Val Thr Asn Val
145                 150                 155                 160

Ala Gly Pro Gly Asp Val Gln Ser Val Ser Ile Lys Gly Ser Ser Thr
                165                 170                 175

Gly Trp Gln Pro Met Ser Arg Asn Trp Gly Gln Asn Trp Gln Ser Asn
            180                 185                 190

Ser Tyr Leu Asp Gly Gln Ser Leu Ser Phe Gln Val Ala Val Ser Asp
            195                 200                 205

Gly Arg Thr Val Thr Ser Asn Asn Val Val Pro Ala Gly Trp Gln Phe
            210                 215                 220

Xaa Gln Thr Phe Glu Gly Gly Gln Phe
225                 230

<210> SEQ ID NO 13
<211> LENGTH: 232
<212> TYPE: PRT
<213> ORGANISM: Plant/eukaryotic
<220> FEATURE:
<221> NAME/KEY: VARIANT
<222> LOCATION: (1)...(232)
<223> OTHER INFORMATION: Xaa = Any Amino Acid

<400> SEQUENCE: 13

Cys Lys Xaa Ser Val Ala Gln Ser Ala Phe Ala Thr Phe Tyr Gly Gly
 1               5                  10                  15

Lys Asp Gly Ser Cys Thr Met Gly Gly Ala Cys Gly Tyr Gly Asn Leu
             20                  25                  30

Tyr Asn Ala Gly Tyr Gly Leu Tyr Asn Ala Ala Leu Ser Ser Ala Leu
             35                  40                  45

Phe Asn Asp Gly Ala Met Cys Gly Ala Cys Tyr Thr Ile Thr Cys Asp
 50                  55                  60

Thr Ser Gln Thr Lys Trp Cys Lys Pro Gly Gly Asn Ser Ile Thr Ile
65                  70                  75                  80

Thr Ala Thr Asn Leu Cys Pro Pro Asn Trp Ala Leu Pro Ser Asn Ser
                 85                  90                  95
```

```
Gly Gly Trp Cys Asn Pro Pro Leu Gln His Phe Asp Met Ser Gln Pro
            100                 105                 110

Ala Trp Glu Asn Ile Ala Val Tyr Gln Ala Gly Ile Val Pro Val Asn
        115                 120                 125

Tyr Lys Arg Val Pro Cys Gln Arg Ser Gly Gly Ile Arg Phe Ala Ile
    130                 135                 140

Gly His Asp Tyr Phe Glu Leu Val Thr Val Thr Asn Val Gly Gly Ser
145                 150                 155                 160

Gly Val Val Ala Gln Met Ser Ile Lys Gly Ser Asn Thr Gly Trp Met
                165                 170                 175

Ala Met Ser Arg Asn Trp Gly Ala Asn Trp Gln Ser Asn Ala Tyr Leu
            180                 185                 190

Ala Gly Gln Ser Leu Ser Phe Ile Val Gln Leu Asp Asp Gly Arg Lys
        195                 200                 205

Val Thr Ala Trp Asn Val Ala Pro Ser Asn Trp Phe Phe Gly Ala Thr
    210                 215                 220

Tyr Ser Thr Ser Trp Val Gln Phe
225                 230

<210> SEQ ID NO 14
<211> LENGTH: 237
<212> TYPE: PRT
<213> ORGANISM: Plant/eukaryotic

<400> SEQUENCE: 14

Arg Ile Pro Gly Arg Tyr Thr Gly Gly Pro Trp Thr Ser Ala His Ala
1               5                   10                  15

Thr Phe Tyr Gly Gly Ser Asp Ala Ser Gly Thr Met Gly Gly Ala Cys
            20                  25                  30

Gly Tyr Gly Asn Leu Tyr Ser Gln Gly Tyr Gly Val Asn Thr Ala Ala
        35                  40                  45

Leu Ser Thr Ala Leu Phe Asn Asn Gly Leu Ser Cys Gly Ala Cys Phe
50                  55                  60

Glu Leu Lys Cys Asp Gln Asp Pro Arg Trp Cys Asn Pro Gly Asn Pro
65                  70                  75                  80

Ser Ile Leu Ile Thr Ala Thr Asn Phe Cys Pro Pro Asn Phe Ala Glu
                85                  90                  95

Pro Ser Asp Asn Gly Gly Trp Cys Asn Pro Pro Arg Pro His Phe Asp
            100                 105                 110

Leu Ala Met Pro Met Phe Leu Lys Ile Ala Gln Tyr Arg Ala Gly Ile
        115                 120                 125

Val Pro Val Ala Tyr Arg Arg Val Pro Cys Arg Lys Ala Gly Gly Ile
    130                 135                 140

Arg Phe Thr Ile Asn Gly Phe Arg Tyr Phe Asn Leu Val Leu Ile Thr
145                 150                 155                 160

Asn Val Ala Gly Ala Gly Asp Ile Val Arg Val Ser Val Lys Gly Thr
                165                 170                 175

Asn Thr Ala Trp Met Thr Met Ser Arg Asn Trp Gly Gln Asn Trp Gln
            180                 185                 190

Ser Asn Ala Val Phe Val Gly Gln Ala Leu Ser Phe Arg Val Thr Gly
        195                 200                 205

Ser Asp Arg Arg Thr Ser Thr Ser Trp Asn Val Ala Pro Pro His Trp
    210                 215                 220

Gln Phe Gly Gln Thr Phe Thr Gly Lys Asn Phe Arg Val
```

```
                225                 230                 235

<210> SEQ ID NO 15
<211> LENGTH: 58
<212> TYPE: PRT
<213> ORGANISM: Plant/eukaryotic

<400> SEQUENCE: 15

Gly Gly Gly Ala Cys Gly Tyr Thr Thr Gly Cys Gly Cys Phe Glu Cys
 1               5                  10                  15

Cys Pro His Phe Asp Ala Phe Lys Ala Gly Phe Arg Arg Val Lys Cys
            20                  25                  30

Lys Gly Lys Thr Asn Leu Val Gly Gly Asp Val Val Ile Lys Trp Trp
        35                  40                  45

Gly Trp Gly Glu Gly Thr Thr Pro Trp Tyr
    50                  55

<210> SEQ ID NO 16
<211> LENGTH: 9
<212> TYPE: PRT
<213> ORGANISM: Plant/eukaryotic

<400> SEQUENCE: 16

Thr Ser Gly Gly Ala Cys Gly Phe Gly
 1               5

<210> SEQ ID NO 17
<211> LENGTH: 9
<212> TYPE: PRT
<213> ORGANISM: Plant/eukaryotic

<400> SEQUENCE: 17

Thr Met Gly Gly Ala Cys Gly Tyr Gly
 1               5

<210> SEQ ID NO 18
<211> LENGTH: 6
<212> TYPE: PRT
<213> ORGANISM: Plant/eukaryotic

<400> SEQUENCE: 18

Tyr Arg Arg Val Gln Cys
 1               5

<210> SEQ ID NO 19
<211> LENGTH: 6
<212> TYPE: PRT
<213> ORGANISM: Plant/eukaryotic

<400> SEQUENCE: 19

Tyr Arg Arg Val Pro Cys
 1               5

<210> SEQ ID NO 20
<211> LENGTH: 6
<212> TYPE: PRT
<213> ORGANISM: Plant/eukaryotic

<400> SEQUENCE: 20

Phe Arg Arg Val Pro Cys
 1               5

<210> SEQ ID NO 21
```

```
<211> LENGTH: 22
<212> TYPE: PRT
<213> ORGANISM: Trichoderma reesei

<400> SEQUENCE: 21

Gly Gly Pro Tyr Tyr Phe Ala Leu Thr Ala Val Asn Thr Asn Gly Pro
 1               5                  10                  15

Gly Ser Val Thr Lys Ile
            20

<210> SEQ ID NO 22
<211> LENGTH: 22
<212> TYPE: PRT
<213> ORGANISM: Homo sapiens

<400> SEQUENCE: 22

Gly Asn Glu Tyr Tyr Phe Arg Val Thr Ala Val Asn Glu Tyr Gly Pro
 1               5                  10                  15

Gly Val Pro Thr Asp Val
            20

<210> SEQ ID NO 23
<211> LENGTH: 18
<212> TYPE: PRT
<213> ORGANISM: Trichoderma reesei

<400> SEQUENCE: 23

Thr Lys Gly Ser Val Thr Ala Ser Trp Thr Asp Pro Met Glu Thr Leu
 1               5                  10                  15

Gly Ala

<210> SEQ ID NO 24
<211> LENGTH: 18
<212> TYPE: PRT
<213> ORGANISM: Homo sapiens

<400> SEQUENCE: 24

Thr Lys Gly Ser Met Leu Val Ser Trp Thr Pro Pro Leu Asp Asn Gly
 1               5                  10                  15

Gly Ser

<210> SEQ ID NO 25
<211> LENGTH: 36
<212> TYPE: DNA
<213> ORGANISM: Artificial Sequence
<220> FEATURE:
<223> OTHER INFORMATION: primer

<400> SEQUENCE: 25
cattagatct cagcaatggc tggtaagctt atcctc                          36

<210> SEQ ID NO 26
<211> LENGTH: 38
<212> TYPE: DNA
<213> ORGANISM: Artificial Sequence
<220> FEATURE:
<223> OTHER INFORMATION: primer

<400> SEQUENCE: 26
cgactctaga aggattagtt ctggctaaac tgcacacc                        38

<210> SEQ ID NO 27
<211> LENGTH: 73
```

```
<212> TYPE: DNA
<213> ORGANISM: Artificial Sequence
<220> FEATURE:
<223> OTHER INFORMATION: synthetic

<400> SEQUENCE: 27
gaagtgcttc ctccctttta gacgcaactg agagcctgag cttcatcccc agcatcatta      60
gatctcagca atg                                                         73

<210> SEQ ID NO 28
<211> LENGTH: 32
<212> TYPE: DNA
<213> ORGANISM: Artificial Sequence
<220> FEATURE:
<223> OTHER INFORMATION: synthetic

<400> SEQUENCE: 28
taatccttct agagtcgacc gcgacggtga cc                                    32

<210> SEQ ID NO 29
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 29
ggcgagatct tgctgcccat catattgtgc                                       30

<210> SEQ ID NO 30
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 30
ggcgtctaga ctgcacacca atgtcaatgt                                       30

<210> SEQ ID NO 31
<211> LENGTH: 37
<212> TYPE: DNA
<213> ORGANISM: Artificial Sequence
<220> FEATURE:
<223> OTHER INFORMATION: primer

<400> SEQUENCE: 31
gcgcagatct cagcaatggc tggtaagctt atcctcg                               37

<210> SEQ ID NO 32
<211> LENGTH: 34
<212> TYPE: DNA
<213> ORGANISM: Artificial Sequence
<220> FEATURE:
<223> OTHER INFORMATION: primer

<400> SEQUENCE: 32
gcgctctaga tcaattctgg ctaaactgca cacc                                  34

<210> SEQ ID NO 33
<211> LENGTH: 9
<212> TYPE: PRT
<213> ORGANISM: Trichoderma reesei

<400> SEQUENCE: 33
```

```
Thr Ser Gly Gly Ala Cys Gly Phe Gly
  1               5

<210> SEQ ID NO 34
<211> LENGTH: 9
<212> TYPE: PRT
<213> ORGANISM: Plant/eukaryotic

<400> SEQUENCE: 34

Thr Met Gly Gly Ala Cys Gly Tyr Gly
  1               5

<210> SEQ ID NO 35
<211> LENGTH: 9
<212> TYPE: PRT
<213> ORGANISM: Artificial Sequence
<220> FEATURE:
<221> NAME/KEY: VARIANT
<222> LOCATION: (2)...(2)
<223> OTHER INFORMATION: Xaa = Met or Ser
<221> NAME/KEY: VARIANT
<222> LOCATION: (8)...(8)
<223> OTHER INFORMATION: Xaa = Tyr or Phe
<220> FEATURE:
<223> OTHER INFORMATION: synthetic oligonucleotide

<400> SEQUENCE: 35

Thr Xaa Gly Gly Ala Cys Gly Xaa Gly
  1               5

<210> SEQ ID NO 36
<211> LENGTH: 6
<212> TYPE: PRT
<213> ORGANISM: Trichoderma reesei

<400> SEQUENCE: 36

Tyr Arg Arg Val Gln Cys
  1               5

<210> SEQ ID NO 37
<211> LENGTH: 6
<212> TYPE: PRT
<213> ORGANISM: Plant/eukaryotic

<400> SEQUENCE: 37

Tyr Arg Arg Val Pro Cys
  1               5

<210> SEQ ID NO 38
<211> LENGTH: 6
<212> TYPE: PRT
<213> ORGANISM: Plant/eukaryotic

<400> SEQUENCE: 38

Phe Arg Arg Val Pro Cys
  1               5

<210> SEQ ID NO 39
<211> LENGTH: 6
<212> TYPE: PRT
<213> ORGANISM: Artificial Sequence
<220> FEATURE:
<221> NAME/KEY: VARIANT
<222> LOCATION: (1)...(1)
<223> OTHER INFORMATION: Xaa = Phe or Tyr
<221> NAME/KEY: VARIANT
<222> LOCATION: (5)...(5)
<223> OTHER INFORMATION: Xaa = Phe or Gln
```

```
<220> FEATURE:
<223> OTHER INFORMATION: synthetic oligonucleotide

<400> SEQUENCE: 39

Xaa Arg Arg Val Xaa Cys
 1               5

<210> SEQ ID NO 40
<211> LENGTH: 32
<212> TYPE: DNA
<213> ORGANISM: Artificial Sequence
<220> FEATURE:
<223> OTHER INFORMATION: synthetic stop codon

<400> SEQUENCE: 40
taatccttct agagtcgacc gcgacggtga cc                              32
```